(12) United States Patent
Lintner

(10) Patent No.: US 6,974,799 B2
(45) Date of Patent: Dec. 13, 2005

(54) COMPOSITIONS CONTAINING MIXTURES OF TETRAPEPTIDES AND TRIPEPTIDES

(75) Inventor: Karl Lintner, Rambouillet (FR)

(73) Assignee: Sederma S.A.S. (FR)

(*) Notice: Subject to any disclaimer, the term of this patent is extended or adjusted under 35 U.S.C. 154(b) by 0 days.

(21) Appl. No.: 10/731,921

(22) Filed: Dec. 10, 2003

(65) Prior Publication Data

US 2004/0132667 A1 Jul. 8, 2004

Related U.S. Application Data

(63) Continuation of application No. PCT/EP03/14019, filed on Nov. 17, 2003.

(51) Int. Cl.[7] .................. A61K 38/06; A61K 38/07; A61K 38/00
(52) U.S. Cl. .................. 514/18; 514/2; 530/300; 530/330; 530/331; 530/345
(58) Field of Search .................. 514/2, 18; 530/300, 530/330, 331, 345

(56) References Cited

U.S. PATENT DOCUMENTS

| 4,686,282 | A | * | 8/1987 | Hahn .................. 530/327 |
| 6,492,326 | B1 | | 12/2002 | Robinson et al. |
| 6,596,761 | B2 | * | 7/2003 | Lanzendorfer et al. ..... 514/456 |
| 6,620,419 | B1 | | 9/2003 | Lintner |
| 2002/0132485 | A1 | * | 9/2002 | Miller et et. .................. 514/458 |
| 2004/0120918 | A1 | * | 6/2004 | Lintner et al. ............ 424/70.14 |

FOREIGN PATENT DOCUMENTS

| DE | 42 44 418 | | 12/1992 | |
| EP | 0 228 868 | | 7/1987 | |
| EP | 0 330 369 | | 8/1989 | |
| GB | 2 274 585 | | 8/1994 | |
| JP | 02240009 | A | * 9/1990 | ............ A61K/7/00 |
| JP | 04356424 | A | * 12/1992 | .......... A61K/35/78 |
| JP | 2000319154 | A | * 11/2000 | ............ A61K/7/40 |
| WO | WO-91/16034 | | 10/1991 | |
| WO | WO-91/16035 | | 10/1991 | |
| WO | WO-95/07432 | | 3/1995 | |
| WO | WO-95/23780 | | 9/1995 | |
| WO | WO-95/34280 | | 12/1995 | |
| WO | WO-96/33689 | | 10/1996 | |
| WO | WO-97/05856 | | 2/1997 | |
| WO | WO-97/21423 | | 6/1997 | |
| WO | WO 97/39733 | | 10/1997 | |
| WO | WO-98/05299 | | 2/1998 | |
| WO | WO-98/07744 | | 2/1998 | |
| WO | WO-98/43607 | | 10/1998 | |
| WO | WO-99/18927 | | 4/1999 | |
| WO | WO-99/25369 | | 5/1999 | |
| WO | WO-99/40897 | | 8/1999 | |
| WO | WO-00/43417 | | 1/2000 | |
| WO | WO-01/43701 | | 11/2000 | |
| WO | WO-01/62218 | | 8/2001 | |
| WO | WO-02/15871 | | 8/2001 | |
| WO | WO-03/028692 | | 10/2001 | |
| WO | WO-02/06668 | | 2/2002 | |
| WO | WO-03/017966 | | 8/2002 | |
| WO | WO 03/068141 | | 8/2003 | |

OTHER PUBLICATIONS

JD McBride and RJ Leatherbarrow. Synthetic peptide mimics of the Bowman–Birk Inhibitor Protein. (2001) Current Medicinal Chemistry, 8, 909–917.*
Renaissance vs. The Competition, (2001 ©). Accessed Aug. 25, 2004 at http://www.spectrum–nutrition.com/level.itml/icoid/1203.1–2.*
Renaissance Cream. Accessed Aug. 25, 2004 at http://www.a–world–of–perfumes–cosmetics.com/stretch_mark_removal_renaissance.htm. 1–3.*
Chemical Information "Rutin". Accessed Aug. 25, 2004 at http://www.ars–grin.gov:8080/npgspub/xsql/duke/chemdisp.xsql?chemical=RUTIN. 1–6.*
Farmacy Query "Coneflower". Accessed Aug. 25, 2004 at http://www.ars–grin.gov/cgi–bin/duke/farmacy2.pl. 1–5.*
"Revitacil". Accessed Aug. 25, 2004 at http://www.heranswer.com/revitacil–study.asp.*
Derwent English Abstract corresponding to DE 42 44 418 A1 (QUELLE). 2 pages.*
Lintner & Peschard, "Biologically active peptides: from a laboratory bench curiosity to a functional skin care porduct," 22Int'l J. Cosmetic Sci. 207–18 (2000).

* cited by examiner

Primary Examiner—Bruce R. Campbell
Assistant Examiner—Andrew D. Kosar
(74) Attorney, Agent, or Firm—Lerner, David, Littenberg, Krumholz & Mentlik, LLP

(57) ABSTRACT

Pharmaceutical, personal care and cosmetic compositions containing a tripeptide and a tetrapeptide are useful for treating visible signs of aging including wrinkles, stretch marks and dark circles.

14 Claims, No Drawings

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Lys Pro Arg
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Lys Pro Arg
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of lipid
      group attachments and preferred embodiments

<400> SEQUENCE: 3

Gly Gln Pro Arg
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Gln Thr Arg
  1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of lipid
```

-continued group attachments and preferred embodiments

<400> SEQUENCE: 5

Lys Thr Thr Lys Ser
 1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Gly Gly Phe
 1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gly Asp Ser
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Arg Lys
 1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Met or Leu
<220> FEATURE:
<223> OTHER INFORMATION: see specification as filed for detailed
      description of lipid
      group attachments and preferred embodiments

<400> SEQUENCE: 9

Tyr Gly Gly Phe Xaa
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
-continued

<220> FEATURE:
<223> OTHER INFORMATION: see specification as filed for detailed
      description of lipid
      group attachments and preferred embodiments

<400> SEQUENCE: 10

Val Gly Val Ala Pro Gly
 1               5
```

COMPOSITIONS CONTAINING MIXTURES OF TETRAPEPTIDES AND TRIPEPTIDES

CROSS REFERENCE TO RELATED APPLICATIONS

This application is a continuation of PCT Application No. PCT/EP 03/14019, designating the U.S., filed Nov. 17, 2003, the disclosure of which is incorporated herein by reference.

BACKGROUND OF THE INVENTION

The first visible signs of aging are usually found on the skin: dryness, fine lines and wrinkles, age spots, red blotches, sagging and flaccid skin. Dullness and loss of hair are also well-known symptoms. Numerous skin or hair care products are available to consumers for treatment or prevention of these skin conditions that are caused by various external sources of stress, including, without limitation, atmospheric pollution, mechanical stress, contact with household and other chemicals and sun exposure (photoaging) including sunburns. This is of course in addition to natural stresses such as acne, diet and general aging.

Skin is perpetually exposed to these stresses, which result in visible signs of skin aging and damage, such as wrinkling and dryness, thinning of the skin and other histological changes. As the skin ages, there is a reduction in protein synthesis, an increase in proteolysis and a general disruption of the skin barrier, connective tissue and cohesion.

Many compounds have been described as being useful for improving skin appearance and physiology, including reducing fine lines, wrinkles and other symptoms associated with aged or photodamaged skin. Many compositions are available on the world wide market. But improvement is always desirable.

Retinoids, alpha and beta-hydroxy acids, flavonoids and Isoflavones are proposed to act against acne and wrinkles, to speed cell renewal, to correct hormonal imbalances. These remedies are not without problems, such as instability (retinoids, flavonoids), irritation (retinoids, hydroxyacids) and potential side effects (phytoflavones).

International Patent Appln. No. WO 00/43,417, published Jul. 27, 2000, assigned to SEDERMA, discloses the use of certain peptides and derivatives as cosmetics or pharmaceutical compositions for the regulation of impaired immunologic functions and inflammation of the skin. The peptides and derivatives described have between 2 and 5 amino acids in length. These peptides and derivatives are said to act by reducing the tissue concentrations of IL-6 and IL-8 to levels close to those observed in young tissues. Exemplified peptides include N-Palmitoyl-Pro-Arg, N-Palmitoyl-Thr-Lys-Pro-Arg (SEQ ID NO: 1), Arg-Lys-Pro-Arg (SEQ ID NO: 2) and N-Palmitoyl-Gly-Gln-Pro-Arg (SEQ ID NO: 3). While combinations of various peptides in accordance with WO 00/43,417 are possible, the reference does not specifically identify a combination of a tripeptide and a tetrapeptide. See also U.S. Pat. Nos. 6,620,419 and 6,492,326 disclosing cosmetic and personal care product incorporating, inter alia, certain tetrapeptides.

SEDERMA also sells a product under the trade name EYELISS to treat bags under the eyes. This product includes a mixture of N-PalmitoylGly-Gln-Pro-Arg (SEQ ID NO: 3) and the dipeptide Val-Trp. This dipeptide has no significant collagen stimulating activity and the combination does not exhibit any enhancement in this property over the levels realized by the use of the tetrapeptide alone. See also JP 07/324,097 and JP 08/311,098 to Daicel Chem, Ind. Ltd., as well as Kawamoto Takafumi et al., Chemical Abstracts, Vol. 124, No. 19, 6 May 1996 (Abstract No. 261765).

SUMMARY OF THE INVENTION

Surprisingly, it has now been found that compositions containing certain tetrapeptides, particularly those of the sequence Gly-Gln-Pro-Arg (SEQ ID NO: 3), its analogs and derivatives, (collectively "rigin-based tetrapeptides"), in combination with one or more tripeptides, particularly those of the sequences Gly-His-Lys, its analogs and derivatives (collectively "GHK-tripeptides"), optionally in combination with one or more additional ingredients (which can include carriers), may, in certain circumstances, provide relief from one or more of the cited symptoms.

It has also been found that the use of tetrapeptides having at least one amino acid including an aliphatic group side chain, at least one amino acid including at least one $NH_2$-containing side chain, and at least one, and preferably two amino acid(s) including at least one cationic amine ($NH_3^+$, $NH_2^+$, etc.—basic amino acids which are positively charged at pH 6.0) containing side chain, as well as acyl derivatives of these (collectively "ALAMCAT-tetrapeptides"), can offer advantages when used in combination with certain tripeptides. Unlike the rigin-based tetrapeptides described above, these ALAMCAT-tetrapeptides, are not necessarily based on rigin, an analog thereof, or a derivative of rigin. However, some of the rigin-based tetrapeptides may fall within this definition just as some ALAMCAT-tetrapeptides will fall within the definition of rigin-based peptides.

The preferred tripeptides in accordance with this aspect of the invention include at least one His (referred to herein as "His-based tripeptides"). Unlike the GHK-tripeptides described above, these His-based tripeptides are not necessarily based on a tripeptide having the sequence Gly-His-Lys, an analog thereof, or a derivative thereof. However, some of the His-based tripeptides may fall within this definition just as some of these GHK-tripeptides will fall within the definition of His-based peptides. These ALAMCAT-tetrapeptides and His-based tripeptides may be used in the same amounts, same proportions, mixed with the same additional ingredients and used the same ways (reducing visible signs of aging, etc.) as the mixtures including rigin-based tetrapeptides and the GHK-tripeptides. Indeed, while it is possible, in accordance with one aspect of the present invention, to combine ALAMCAT-tetrapeptides with His-based tripeptides or combine rigin-based tetrapeptides with GHK-tripeptides as discussed above, combinations of ALAMCAT-tetrapeptides with GHK-tripeptides as well as rigin-based tetrapeptides with His-based tripeptides are also contemplated. Therefore, while aspects of the invention will often be described in terms of "tetrapeptides" and mixtures with certain "tripeptides" those descriptions may be applied equally to all of the above, unless specified otherwise.

In particular, it was discovered that repeated topical application of some combinations of tetrapeptides (rigin-based tetrapeptides, ALAMCAT-tetrapeptides or mixtures thereof) with tripeptides (His-based tripeptides, GHK-tripeptides or mixtures thereof) can offer at least some of the advantages and qualities described herein as well as others which can be derived by routine analysis thereof. These advantages may include, but are not limited to, the ability, in some cases and with certain preferred combinations, to improve the visible signs of aging in human skin, including fine lines, wrinkles, enlarged pores, roughness, dryness, and other skin texture defects such as stretch marks (as caused by pregnancy, trauma or other influences, bags under the eyes, also called "puffy eyes" and dark (under eye) circles, both caused by thinning of the skin, insufficient blood circulation and slack tissue. Indeed, some of these compositions have been discovered to have a benefit in tissue regeneration. Some combinations of tetrapeptides and tripeptides in accordance with the present invention can stimulate the production of certain advantageous biomolecules, such as, without limitation, collagen I, fibronectin, collagen IV and hyaluronic acid, in skin cells. In some instances, the combination will stimulate production of a biomolecule where application of either of the tetrapeptide or tripeptide alone would not. In other instances, the combination stimulates production of a greater amount of a biomolecule than achieved from the peptides individually when added. Indeed, in certain preferred aspects of the present invention, a synergistic combination is produced.

In one aspect, the present invention relates to topical compositions containing mixed tetrapeptides and tripeptides, optionally formulated in combination with additional skin care actives or additional ingredients which can include a dermatologically acceptable carrier. Particularly preferred are compositions that include a ALAMCAT-tetrapeptide compounded with a His-based tripeptide and compositions that include a rigin-based tetra-peptide compounded with a GHK-tripeptide. A particularly preferred tetrapeptide in accordance with the present invention is N-Palmitoyl-Gly-Gln-Pro-Arg (SEQ ID NO: 3). Particularly preferred tripeptides useful in accordance with the present invention are those based on the amino acid sequence Gly-His-Lys, its analogs and its N-acyl-derivatives such as N-Palmitoyl-Gly-His-Lys.

Certain aspects of the present invention also relate to the use of such compositions to make cosmetics, personal care products, topical pharmaceutical preparation or a medicament for reducing the visible signs of aging of human skin. This is accomplished by topical application of the medicaments of the invention to the skin of the human needing such treatment.

Certain aspects of the present invention also relate to methods of using such compositions to improve the state and appearance of human skin and to prevent and/or reduce the visible signs of aging. These methods generally consist in topically applying the composition to the skin when needed, in the amount and at the frequency best suited for the purpose. Methods of preventing, delaying the onset, or treating a skin condition are also contemplated.

DETAILED DESCRIPTION

All publications cited herein are hereby incorporated by reference in their entirety.

The cosmetic compositions of the present invention contain tetrapeptides, particularly rigin-based tetrapeptides and/or ALAMCAT-tetrapeptides. These are collectively referred to herein as "tetrapeptides" unless the context or the explicit statements indicate otherwise. The cosmetic compositions of the present invention also contain His-based tripeptides and/or GHK-tripeptides. These are collectively referred to herein as "tripeptides" unless the context or the explicit statements indicate otherwise. One or more additional ingredients, including one or more dermatologically acceptable carrier(s) are also preferably used in these compositions.

The term "dermatologically acceptable," as used herein, means that the compositions or components described are suitable for use in contact with human skin without risk of toxicity, incompatibility, instability, allergic response, and the like.

All terms such as "skin aging," "signs of skin aging," "topical application," and the like are used in the sense in which they are generally and widely used in the art of developing, testing and marketing cosmetic and personal care products. The term "cosmetic composition" or more briefly just "composition" in accordance with the present invention relates to a formulation that can be used for cosmetic purposes, purposes of hygiene or as a basis for delivery of one or more pharmaceutical ingredients. It is also possible that these formulations are used for two or more of these same purposes at one time. A medicated dandruff shampoo, for example, has pharmacological properties and is used as a personal care product to provide clean hair. At a minimum, these compositions include a mixture of tri- and tetra-peptides, analogs or derivatives thereof. These compositions may also include additional ingredients such as a dermatologically acceptable carrier.

"Cosmetics," as used herein, include without limitation, lipstick, mascara, rouge, foundation, blush, eyeliner, lipliner, lip gloss, facial or body powder, sunscreens and blocks, nail polish, mousse, sprays, styling gels, nail conditioner, whether in the form of creams, lotions, gels, ointments, emulsions, colloids, solutions, suspensions, compacts, solids, pencils, spray-on formulations, brush-on formulations and the like. Personal care products include, without limitation, bath and shower gels, shampoos, conditioners, cream rinses, hair dyes and coloring products, leave-on conditioners, sunscreens and sunblocks, lip balms, skin conditioners, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, deodorants, cleansers, skin gels, rinses, whether in solid, powder, liquid, cream, gel, ointment, lotion, emulsions, colloids, solutions, suspensions, or other form. Pharmaceutical preparations in accordance with the present invention include, without limitation, carriers for dermatological purposes, including topical and transdermal application of pharmaceutically active ingredients. These can be in the form of gels, patches, creams, nose sprays, ointments, lotions, emulsions, colloids, solutions, suspensions, powders and the like.

The term "tripeptide" in accordance with the present invention is a compound that includes an uninterrupted sequence of three amino acids within its structure. These are indicated herein using a traditional three letter convention from left (N-terminal end) to right (C-terminal end). In this nomenclature, Gly is glycine, His is histidine, Lys is lysine, Pro is proline, Gln is glutamine and Arg is arginine. A "tetrapeptide" in accordance with the present invention is a compound that includes an uninterrupted sequence of four amino acids within its structure.

The term "amino acid" as employed herein includes and encompasses all of the naturally occurring amino acids, either in the D- or L-configuration if optically active, and the known non-native, synthetic, and modified amino acids, such as homocysteine, ornithine, norleucine and p-valine. A list of non natural amino acids may be found in *The Peptides*, Vol. 5 (1983), Academic Press, Chapter VI, by D. C. Roberts and F. Vellaccio. The amino acids in the peptides of the present invention may be present in their natural L-configuration, unnatural D-configuration, or as a racemic mixture.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

As used herein, prophylactically regulating a skin condition includes delaying, minimizing and/or preventing visible and/or tactile discontinuities in skin (e.g., texture irregularities in the skin which may be detected visually or by feel), including signs of skin aging.

As used herein, therapeutically regulating skin condition includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition.

Some of the products and compositions of the present invention are useful for improving skin appearance and/or feel. For example, preferred compositions of the present invention are useful for regulating the appearance of skin condition by providing an immediate visual improvement in skin appearance following application of the composition to the skin. Generally speaking, compositions of the present invention which further contain particulate materials will be most useful for providing the immediate visual improvement.

Some of the compositions of the present invention may also provide additional benefits, including stability, absence of significant (consumer-unacceptable) skin irritation, anti-inflammatory activity and good aesthetics.

In certain preferred aspects, the present invention is useful for improving the physiological state and/or the physical appearance of human skin, in particular to reduce the signs of skin aging that are generated by sun exposure, physical and hormonal stress, abrasion, nutritional effects and other similar causes. The compositions may often be used to prevent the signs of aging and/or to treat them in order to afford the consumer who uses them, a more youthful appearance.

While the specification concludes with the claims particularly pointing and distinctly claiming the invention, it is believed that the present invention will be better understood from the following description. The terms "having" and "including" are to be construed as openended unless the context suggests otherwise.

All percentages and ratios used herein are by weight of the total composition and all measurements made are at 25° C. unless otherwise designated.

The compositions of the present invention can comprise (open ended) or consist essentially of the components of the present invention as well as other ingredients described herein. As used herein, "consisting essentially of" means that the composition or component may include additional ingredients, but only if the additional ingredients do not materially alter the basic and novel characteristics of the claimed compositions or methods. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained.

Tetrapeptides

The cosmetic compositions of the present invention preferably contain a safe and effective amount of at least one tetrapeptide. These may be one or more rigin-based tetrapeptides, one or more ALAMCAT-tetrapeptides or mixtures thereof. These tetrapeptides may be naturally occurring or of synthetic origin.

Rigin-based tetrapeptides in accordance with the present invention are based on the structure Gly-Gln-Pro-Arg (SEQ ID NO: 3) (Rigin) and include its analogs and derivatives thereof.

Rigin is a preferred tetrapeptide. Analogs of the tetrapeptide rigin useful in accordance with the present invention include those in which one or more of the four amino acids are reorganized or rearranged within the sequence and/or where no more than two of the amino acids are substituted (e.g., Ala-Gln-Thr-Arg (SEQ ID NO: 4)). More preferably, at least one of the amino acids within the sequence is Pro or Arg and most preferably the tetrapeptide includes both Pro and Arg although their order and position may vary. The amino acid substitutions can be from amongst any amino acid as defined herein. Particularly preferred rigin-based tetrapeptides include Xaa-Xbb-Arg-Xcc, Xaa-Xbb-Xcc-Pro, Xaa-Xbb-Pro-Arg, wherein Xaa-Xbb-Pro-Xcc, Xaa-Xbb-Xcc-Arg, Xaa, Xbb and Xcc may be the same or different and selected from the following Xaa is Gly or the amino acids that may be substituted therefore, Xbb is Gln or the amino acids that may be substituted therefore and Xcc may be Pro or Arg or the amino acids substituted therefore. The most preferable amino acids substituted for Gly include an aliphatic side chain such as, without limitation, beta-Ala, Ala, Val, Leu, Pro, Sarcosine (Sar) and Ile. The most preferable amino acids substituted for Gln include a side chain that includes an amine group that is predominantly uncharged at neutral pH (pH 6–7) such as, without limitation, Asn, Lys, Orn, 5-hydroxyproline, Citrulline and Canavanine. When Arg is substituted, it is preferrably replaced with an amino acid having a side chain that includes, predominantly, a charged nitrogen at a pH of about 6, such as, without limitation, Pro, Lys, His, Desmosine and Isodesmosine.

Derivatives are also considered to be encompassed by the term rigin-base tetrapeptides in accordance with the present invention, (and therefore also the more generic term tetrapeptides). Derivatives include derivatives of the substituted and rearranged rigin-based tetrapeptides described herein. These derivatives include, inter alia, acyl-derivatives, which are tetrapeptides substituted with one or more straight-chain or branched-chain, long or short chain, saturated or unsaturated, substituted with a hydroxy, amino, amino acyl, sulfate or sulfide group or unsubstituted having from 1 to 29 carbon atoms. N-acyl-derivatives include those acyl groups which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid and the like. Preferable examples of the acyl group include an acetyl group, a palmitoyl group, an elaidoyl group, a myristyl group, a biotinyl group and an octanoyl group. These may be substituted or unsubstituted. When substituted, they are preferably substituted with hydroxyl or, sulphur containing groups such as, without limitation $SO_3H$, SH or S—S.

ALAMCAT tetrapeptides are tetrapeptides which include at least one amino acid including an aliphatic group containing side chain. These amino acids include, without limitation, Gly, beta-Ala, Ala, Val, Leu, Sarcosine (Sar) and Ile. These tetrapeptides also include at least one amino acid including at least one $NH_2$- containing side chain. These amino acids include a side chain that has an amine group that is predominantly uncharged at neutral pH (pH 6–7) such as, without limitation, Gln, Asn, Lys, Orn, 5-hydroxyproline, Citrulline and Canavanine. The ALAMCAT-tetrapeptides also include at least one amino acid having at least one side chain including at least one cationic amine (predominant species is charged such as $NH_3^+$, $NH_2^+$, etc.—basic amino acids which are positively charged at pH about 6.0). These amino acids include, without limitation, Pro, Arg, Lys, His, Desmosine and Isodesmosine. The remaining amino acid can be any amino acid, but is preferably one containing an alphatic group, pendant amino group or pendant cationic group.

Derivatives are also considered to be encompassed by the term ALAMCAT-tetrapeptides in accordance with the present invention, (and therefore also the more generic term tetrapeptides). These derivatives include, inter alia, acyl-derivatives, which are tetrapeptides substituted with one or more straight-chain or branched-chain, substituted or unsubstituted long or short chain, saturated or unsaturated acyl group(s) having from 1 to 29 carbon atoms. The acyl groups which can be used are the same as those described for the rigin-based tetrapeptides.

Preferred embodiments include N-acyl-Gly-Gln-Pro-Arg (SEQ ID NO: 3) peptides, most preferably N-palmitoyl-Gly-Gln-Pro-Arg (SEQ ID NO: 3).

Preferred commercially available sources of tetrapeptides include RIGIN, EYELISS and MATRIXYL RELOADED, MATRIXYL 3000, which contain between 50 to 500 ppm of palmitoyl-Gly-Gln-Pro-Arg (SEQ ID NO: 3), and other ingredients, such as peptides, chalcones and an excipient, commercially available from SEDERMA, France. These may be used to produce compositions of the present invention by adding thereto at least one tripeptide as described herein.

The tetrapeptides of the present invention are preferably used in amounts from about 0.1 ppm (0.00001% w/w also referred to herein as "weight percent", "weight %" or simply by weight) to about 5000 ppm (0.5% w/w), preferably from about 0.5 ppm to about 500 ppm (0.05% w/w), and most preferably from about 1 ppm to about 100 ppm by weight of the composition.

Tripeptides

The cosmetic compositions of the present invention preferably contain a safe and effective amount of a tripeptide. Tripeptides as used herein includes one or more His-based tripeptides, one or more GHK-tripeptides and/or mixtures thereof. These are of course mixed with the tetrapeptides as described herein. These tripeptides may be naturally occurring or of synthetic origin.

Preferred tripeptides in accordance with one aspect of the present invention are based on the structure Gly-His-Lys and its analogs and derivatives thereof. These are collectively known herein as GHK-tripeptides. Indeed, the preferred tripeptide in accordance with this aspect of the invention has this exact sequence of amino acids. Analogs of the preferred tripeptide useful in accordance with the present invention include those in which one or more of the three amino acids are reorganized or rearranged within the sequence (e.g., Gly-Lys-His) and/or where no more than two amino acids are substituted (e.g., His-Ala-Orn) However, most preferably, amino acids substituted for Gly include an aliphatic side chain such as, without limitation, beta-Ala, Ala, Val, Leu, Pro, Sarcosine (Sar) and Ile. Most preferred are Ala, Leu and Ile. The most preferable amino acid substituted for Lys or His include those having a side chain that includes, predominantly, a charged nitrogen at a pH of about 6, such as, without limitation, Pro, Lys, Arg, His, Desmosine and Isodesmosine. Most preferably, Lys is replaced with Orn, Arg, or Citrulline.

Derivatives are also considered to be encompassed by the term GHK-tripeptides in accordance with the present invention, (and therefore also the more generic term tripeptides). Derivatives of GHK-tripeptides in accordance with the present invention include derivatives of the substituted and rearranged tripeptides described herein. These derivatives include, inter alia, acyl-derivatives, which are tripeptides substituted with one or more straight-chain or branched-chain, long or short chain, saturated or unsaturated, substituted with a hydroxy, amino, acyl amino, sulfate or sulfide group, or unsubstituted, which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid and the like. Preferable examples of the acyl group include an acetyl group, a palmitoyl group, an elaidoyl group, a myristyl group, a biotinyl group and an octanoyl group. These may be substituted or unsubstituted. When substituted, they are preferably substituted with hydroxyl or sulphur containing groups such as, without limitation $SO_3H$, SH or S—S.

His-based tripeptides in accordance with the present invention include at least one His. The other two amino acids in the sequence may be the same or different. Thus, contemplated are, without limitation, His-Xaa-Xaa, His-Xaa-Xbb, His-Xbb-Xaa, Xbb-His-Xbb, Xbb-His-Xaa, Xaa-His-Xbb, Xaa-Xaa-His, Xaa-Xbb-His, Xbb-Xaa-His and Xbb-Xbb-His, where Xaa and Xbb are two different amino acids, although either can be His. Preferably, at least one of the other amino acids is Gly, beta-Ala, Ala, Val, Leu, Pro, Sarcosine (Sar) or Ile. Preferably, at least one of the other amino acids is Pro, Lys, Arg, His, Desmosine and Isodesmosine. Most preferably, Lys is replaced with Orn, Arg, or Citrulline.

Derivatives are also considered to be encompassed by the term His-based tripeptides in accordance with the present invention, (and therefore also the more generic term tripeptides). These derivatives include, inter alia, acyl-derivatives, which are tripeptides substituted with one or more straight-chain or branched-chain, long or short chain, saturated or unsaturated substituted or unsubstituted acyl group(s) having from 1 to 29 carbon atoms. The acyl groups which can be used are the same as those described for the GHK-tripeptides.

Particularly preferred embodiments of tripeptides in accordance with the present invention include N-Acyl-Gly-His-Lys and most preferably, N-Palmitoyl-Gly-His-Lys.

Preferred commercially available tripeptide and tripeptide derivative containing compositions include Biopeptide-CL from SEDERMA, Maxilip® from SEDERMA, Biobustyl® from SEDERMA.

The tripeptides of the present invention are preferably used in amounts that can be as little as 0.10 ppm to about 10,000 ppm, preferably between about 0.50 ppm to about 1,000 ppm, more preferably from about 1 ppm to about 500 ppm, and most preferably from about 1 ppm to about 200 ppm. These are again based on a % w/w basis as are the amounts of tetrapeptides. Thus 100,000 ppm is about 10% by weight of the cosmetic composition.

In one preferred aspect of the present invention, there is provided a composition which can include nothing more than a mixture of at least one molecule including a sequence of four amino acids, at least two of the amino acids being selected from Gly, Gln, Pro and Arg and at least one of the amino acids being Arg or Pro, and at least one molecule including a sequence of three amino acids, at least one of the amino acids being His. Optionally at least one of the amino acids is substituted with an acyl group. More preferred are combinations of such mixtures with at least one additional ingredient. These mixtures can be combined with any of the additional ingredients described herein in the amounts described herein in connection with tripeptides and tetrapeptides as described above. Indeed the amounts of these molecules and their relative proportions can be identical to those disclosed herein for tripeptides, tetrapeptides.

More preferably, the molecule including a sequence of four amino acids includes both Pro and Arg and even more preferably at least one of the molecules including a sequence of three or four amino acids includes an amino acid that is substituted with an acyl group. The acyl group is preferably bound to the N-terminal end of at least one amino acid and is a straight-chain or branched-chain, long or short chain, saturated or unsaturated acyl group, which can be derived from acetic acid, biotinic acid, capric acid, lauric acid, myristic acid, octanoic acid, palmitic acid, stearic acid, behenic acid, linoleic acid, linolenic acid, oleic acid, isostearic acid, elaidoic acid, lipoic acid, 2-ethylhexaneic acid, coconut oil fatty acid, tallow fatty acid, hardened tallow fatty acid, palm kernel oil fatty acid, lanolin fatty acid or mixtures thereof. These may be substituted or unsubstituted. When substituted, they are preferably substituted with hydroxyl or sulphur containing groups such as, without limitation $SO_3H$, SH or S—S.

The ratio of tetrapeptide to tripeptide, or indeed the ratio of molecules having four amino acids to those having three amino acids can range from about 100:1 to about 1:100; more preferably from about 50:1 to about 1:50, even more preferably from about 30:1 to about 1:30 and even more preferably between about 10:1 to about 1:10. Most preferably, the ratio of tetrapeptide to tripeptide ranges from between about 3:1 to about 1:3. These ratios are on a weight basis (% w/w—e.g. mg of pure peptide per Kilogram in the final formulation). In a particularly preferred embodiment, the amount of tripeptide used is greater than the amount of tetrapeptide used when considered in terms of their amounts in parts per million, again based on overall weight of the composition.

It has been unexpectedly found that the combination of selected tripeptides and tetrapeptides, as well as their analogs and derivatives, can provide significant advantages compared to products produced from other small peptides, either alone or in combination. For example, a solution having a concentration of 500 ppm of N-Palmitoyl-Gly-Gln-Pro-Arg (SEQ ID NO: 3) is sold under the tradename RIGIN by SEDERMA. As shown in Table 1 at a concentration of 2.5 ppm, this peptide exhibits a small stimulation of collagen I synthesis (+19%) over baseline, which is standard DMEM culture medium. The tripeptide N-Palmitoyl-Gly-His-Lys, when used at a concentration of 5 ppm, double that of the tetrapeptide, provided an even smaller increase (+11%). Yet the combination of these two peptides, in the same amounts produced a significant increase in stimulation of collagen I synthesis (+63%). This is more than double the amount expected based on the additive effect of these peptides.

At a higher concentration, the results are even more profound. The tetrapeptide produced (+65%) increase in synthesis of collagen I at a concentration of 3.64 ppm. At 7.3 ppm, a reduction in synthesis was exhibited. When these two peptides were combined in the same amounts, the result was +256%. At this concentration, unexpected and superior results in terms of fibronectin, collagen IV and hyaluronic acid were also observed.

TABLE 1

Percentage of variation with respect to solvent
(0.08% DMSO in DMEM): 3 × 10E−4% ascorbic acid level.

|  |  | Collagen I | Fibronectin | Collagen IV | Hyaluronic Acid |
|---|---|---|---|---|---|
| TGF-β |  $10^E$−6% | +91%* | +176% | +4% | +43% |
| Pal KTTKS | 1 ppm | +8% | +24% | +6% | +3% |
| (SEQ ID NO: | 2 ppm | +30% | +20 | +12% | +26% |
| 5) | 4 ppm | +48% | +74% | +15% | +28% |
|  | 8 ppm | +93% | +100% | +22% | +31% |
| Pal | 0.5 ppm | +4% | +1% | +5% | −4% |
| GQPR (SEQ ID | 1.5 ppm | −1% | +15% | −8% | +9% |
| NO: 3) | 2.5 ppm | +19% | +35% | −5% | −13% |
|  | 3.64 ppm | +65% | +56% | −14% | −1% |
| Pal GHK | 1 ppm | +9% | +8% | +5% | +3% |
|  | 3 ppm | −11% | +2% | −4% | +11% |
|  | 5 ppm | +11% | −15% | +6% | 0% |
|  | 7.3 ppm | −9% | +13% | −9% | −1% |
| Combination 1 | 1 + 0.5 | +33% | +1% | −4% | +9% |
|  | 3 + 1.5 | +67% | +41% | −10% | +11% |
|  | 5 + 2.5 | +63% | +44% | −5% | +27% |
|  | 7.3 + 3.64 | +256% | +147% | +20% | +92% |

TABLE 1-continued

Percentage of variation with respect to solvent
(0.08% DMSO in DMEM): 3 × 10E–4% ascorbic acid level.

|  |  | Collagen I | Fibronectin | Collagen IV | Hyaluronic Acid |
|---|---|---|---|---|---|
| Acetyl-YGG | 1 ppm | −2% | n.t. | n.t. | n.t. |
|  | 3 ppm | +5% |  |  |  |
|  | 5 ppm | −11% |  |  |  |
| Pal-YGGF (SEQ ID NO: 6) | 1 ppm | +5% | n.t. | n.t. | n.t. |
|  | 3 ppm | −6% |  |  |  |
|  | 5 ppm | +4% |  |  |  |
| Combination 2 | 1 + 0.5 | −7% | n.t. | n.t. | n.t. |
|  | 3 + 1.5 | −5% |  |  |  |
|  | 5 + 2.5 | −13% |  |  |  |
| Oleoyl-RGD | 1 ppm | +5% | n.t. | n.t. | n.t. |
|  | 3 ppm | −3% |  |  |  |
| Oleoyl-RGDS (SEQ ID NO: 7) | 1 ppm | −7% | n.t. | n.t. | n.t. |
|  | 3 ppm | −2% |  |  |  |
| Combination 3 | 1 + 0.5 | −12% | n.t. | n.t. | n.t. |
|  | 3 + 1.5 | −15% |  |  |  |

*percentage increase over baseline

In generating the data in Table 1, normal human skin fibroblasts were cultivated in 24 well-plates in DMEM with 10% of Fetal Calf Serum ("FCS") during 24 h, then rinsed. The cells then received the products to be tested in a medium DMEM without FCS ("Fetal Calf Serum") containing ascorbic acid. The contact of cells with product was carried out during 3 days, then supernatants was taken and frozen. Each test includes a negative control without solvent, a control solvent and a positive control ($10^{-6}$% of Transforming Growth Factor-β ("TGF-β")). Each determination was carried out n=3. Several repetitions independent of the tests can be made. Assaying of the interesting molecules was carried out by Elisa (Collagen I & IV; Fibronectine) or by a colorimetric method (hyaluronic acid). The tripeptide alone has, under these experimental conditions, essentially no effect. The tetrapeptide has stimulating effect, never before shown, at least not to the applicants' knowledge. Most interesting, however is the determination that the combination of the two is not only better than one could even hope based on the addition of tri- and tetra, but also more effective than a commercially successful pentapeptide, MATRIXYL (Pal-KTTKS) (SEQ ID NO: 5) available from SEDERMA. Table 1 also shows that not all tri- and/or tetrapeptides or combinations lead to the observed effect. Tri- and tetrapeptide sequences of different nature (YGG is a fragment of enkephaline, and so is YGGF=Tyr-Gly-Gly-Phe (SEQ ID NO: 6); RGD=Arg-Gly-Asp, a fragment of fibronectin, and RGDS=Arg-Gly-Asp-Ser) (SEQ ID NO: 7) do not show collagen I stimulation, neither alone nor in combination. Higher concentrations were not tested because of cytotoxicity, and the other biomolecules were not assayed (n.t.=not tested) because of the lack of initial response in collagen I stimulation, which is the essential, primary parameter.

In addition, preferred combinations of tetrapeptides and tripeptides in accordance with some aspects of the invention have exhibited powerful anti-wrinkle results as well as benefits in terms of stretch marks (prevention and treatment).

Additional Ingredients

In addition to the tri- and tetrapeptides, analogs and/or derivatives thereof, the compositions of the invention may include various other and additional ingredients, which may be active, functional, conventionally used in cosmetic, personal care or topical/transdermal pharmaceutical products or otherwise. Of course, a decision to include an additional ingredient and the choice of specific additional ingredients depends on the specific application and product formulation. Also, the line of demarcation between an "active" ingredient and an "inactive ingredient" is artificial and dependent on the specific application and product type. A substance that is an "active" ingredient in one application or product may be a "functional" ingredient in another, and vice versa. A particular ingredient might provide substantivity in one formulation, facilitate transdermal application in another, and merely provide proper viscosity in a third. Which of these is functional and which is active is subject to debate. But, regardless of the outcome, the material in question would qualify as an additional ingredient in accordance with the present invention.

Thus, the compositions of the invention may include one or more additional ingredients, which provide some benefit to the object of the composition. Such additional ingredients may include one or more substances such as, without limitations, cleaning agents, hair conditioning agents, skin conditioning agents, hair styling agents, antidandruff agents, hair growth promoters, perfumes, sunscreen and/or sunblock compounds, pigments, moisturizers, film formers, hair colors, make-up agents, detergents, pharmaceuticals, thickening agents, emulsifiers, humectants, emollients, antiseptic agents, deodorant actives, dermatologically acceptable carriers and surfactants.

The compositions of the present invention generally contain at least one additional ingredient. The compositions of the present invention may contain a plurality of additional ingredients as well.

In a preferred embodiment, where the composition is to be in contact with human keratinous tissue, the additional ingredients should be suitable for application to keratinous tissue, that is, when incorporated into the composition they are suitable for use in contact with human keratinous tissue (hair, nails, skin, lips) without undue toxicity, incompatibility, instability, allergic response, and the like within the scope of sound medical judgment. The *CTFA Cosmetic Ingredient Handbook*, Ninth Edition (2002) describes a wide variety of nonlimiting cosmetic and pharmaceutical ingredients commonly used in the skin care industry, which are suitable for use as additional ingredients in the compositions of the present invention. Non-limiting examples of these additional ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof. Further skin care and hair care active ingredients that are particularly useful in combination with the tri/tetrapeptide mixture can be found in SEDERMA commercial literature and on the website www.sederma.fr. (herewith incorporated in its entirety).

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

Farnesol

The topical compositions of the present invention may contain a safe and effective amount of farnesol. Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E, 6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco, 10 Gordon Drive, Totowa, N.J.) and trans-trans-farnesol (Sigma Chemical Company, P.O. Box 14508, St. Louis, Mo.).

When present in the compositions of the present invention, the composition preferably contains from about 0.001% to about 50%, by weight of the composition, more preferably from about 0.01% to about 20%, even more preferably from about 0.1% to about 15%, even more preferably from about 0.1% to about 10%, still more preferably from about 0.5% to about 5%, and still more preferably from about 1% to about 5% of farnesol.

Phytantriol

The topical compositions of the present invention may contain a safe and effective amount of phytantriol. Phytantriol is the common name for the chemical known as 3,7,11,15, tetramethylhexadecane-1,2,3, -triol. Phytantriol is commercially available from BASF (1609 Biddle Avenue, Wyandotte, Mich.). For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

In the compositions of the present invention, the phytantriol is preferably included in an amount from about 0.001% to about 50% by weight of the composition, more preferably from about 0.01% to about 20%, even more preferably from about 0.1% to about 15%, even more preferably from about 0.2% to about 10%, still more preferably from about 0.5% to about 10%, and still more preferably from about 1% to about 5%.

Desquamation Actives

A safe and effective amount of a desquamation active may be added to the compositions of the present invention, more preferably from about 0.1% to about 10%, even more preferably from about 0.2% to about 5%, also preferably from about 0.5% to about 4%, by weight of the composition. Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Another desquamation system that is suitable for use herein contains salicylic acid and zwitterionic surfactants and is described in U.S. Pat. No. 5,652,228 to Bissett, incorporated herein by reference. Zwitterionic surfactants such as described in these applications are also useful as desquamatory agents herein, with cetyl betaine being particularly preferred.

Enzymes, Enzyme Inhibitors and Enzyme Activators (Coenzymes)

The compositions of the present invention may contain a safe and effective amount of one or more enzymes, enzyme inhibitors or enzyme activators (coenzymes). Examples of enzymes are lipases, proteases, catalase, superoxide-dismutase, amylases, glucuronidases, peroxidases, in particular glutathione peroxidase or lactoperoxidase, ceramidases, hyaluronidases. All of these enzymes may be obtained by extraction or by fermentation biotechnology processes. Examples of enzyme inhibitors include trypsin inhibitors, Bowmann Birk inhibitor, chymotrypsin inhibitors, botanical extracts with or without tannins, flavonoids, quercetin which inhibit enzymatic activity. Enzyme preparations can be found, for instance, in the product named VENUCEANE proposed by SEDERMA, France (WO 02/066668 of Aug. 28, 2002). Enzyme activators and coenzymes include Coenzyme A, coenzyme Q10 (ubiquinone), glycyrrhizidine, berberine, chrysine.

Botanical Extracts and Marine Extracts

The compositions of the present invention may contain a safe and effective amount of one or more extracts obtained from vegetable or marine sources. These extracts may be obtained by standard extraction processes, and be used in powder, paste, balm, oil, or liquid (i.e., solution) form, preferentially as hydroglycolic extracts of terrestrial plants or marine plants, such as seaweeds, algae, microalgae. These botanical and marine extracts possess various properties well known in cosmetic usage and may be advantageously combined with the tri/tetrapeptide combination object of this patent: soothing and anti-inflammatory, enzyme inhibition, moisturizing, anti-wrinkle, hormone replacement, anti-oxidant, emollient, seboregulating, anti-hairloss, hair growth promoting, anti-cellulite, skin healing, skin whitening, lipolytic, tanning, anti-microbial and the like.

Anti-Acne Actives

The compositions of the present invention may contain a safe and effective amount of one or more anti-acne actives. Examples of useful anti-acne actives include resorcinol, sulfur, salicylic acid, benzoyl peroxide, erythromycin, zinc, etc. Further examples of suitable anti-acne actives are described in further detail in U.S. Pat. No. 5,607,980, issued to McAtee et al., on Mar. 4, 1997. Especially useful are combinations with the anti-acne ingredient called "ac.net" offered by SEDERMA and described in WO 03/028692 A2 of Apr. 10, 2003.

Anti-Wrinkle Actives/Anti-Atrophy Actives

The compositions of the present invention may further contain a safe and effective amount of one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, skin peel agents (e.g., phenol and the like), vitamin $B_3$ compounds and retinoids which enhance the keratinous tissue appearance benefits of the present invention, especially in regulating keratinous tissue condition, e.g., skin condition. Especially useful are combinations with the wrinkle agents called Dermolectine and Sterocare offered by SEDERMA, the latter described in WO99/18927 of Apr. 22, 1999.

a) Vitamin $B_3$ Compounds

The compositions of the present invention may contain a safe and effective amount of a vitamin $B_3$ compound. Vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997). When vitamin $B_3$ compounds are present in the compositions of the instant invention, the compositions preferably contain from about 0.01% to about 50%, more preferably from about 0.1% to about 10%, even more preferably from about 0.5% to about 10%, and still more preferably from about 1% to about 5%, still more preferably from about 2% to about 5%, by weight of the composition, of the vitamin $B_3$ compound.

As used herein, "vitamin $B_3$ compound" means a compound having the formula:

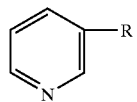

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

b) Retinoids

The compositions of the present invention may also contain a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%.

Where the compositions of the present invention contain both a retinoid and a Vitamin $B_3$ compound, the retinoid is preferably used in the above amounts, and the vitamin $B_3$ compound is preferably used in an amount of from or about 0.1% to or about 10%, more preferably from or about 2% to or about 5%.

Hydroxy Acids

The compositions of the present invention may contain a safe and effective amount of a hydroxy acid. Preferred hydroxy acids for use in the compositions of the present invention include salicylic acid and salicylic acid derivatives. When present in the compositions of the present invention, salicylic acid is preferably used in an amount of from about 0.01% to about 50%, more preferably from about 0.1% to about 20%, even more preferably from about 0.1% to about 10%, still more preferably from about 0.5% to about 5%, and still more preferably from about 0.5% to about 2%.

Peptides

Additional peptides, including but not limited to, di-, tri-, tetra-, penta- and hexapeptides and derivatives thereof, may be included in the compositions of the present invention in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine (beta-Ala-His). Suitable tripeptides for use herein include Arg-Lys-Arg, His-Gly-Gly. Preferred tripeptides and derivatives thereof include N-Palmitoyl-Gly-Lys-His, which may be purchased from Sederma, France); PEPTIDE CK (Arg-Lys-Arg); PEPTIDE CK+(ac-Arg-Lys-Arg-$NH_2$); and a copper derivative of His-Gly-Gly sold commercially as LAMIN, from Sigma (St. Louis, Mo.). Suitable tetrapeptides for use herein include PEPTIDE E, Arg-Ser-Arg-Lys (SEQ ID NO: 8). Other suitable peptides for use herein include, but are not limited to Tyr-Arg, Val-Trp, Asn-Phe, Asp-Phe, N-Palmitoyl-beta-Ala-His, N-Acetyl-Tyr-Arg-hexadecylester, and derivatives thereof, Lys-Phe-Lys, N-Elaidoyl-Lys-Phe-Lys and its analogs of conservative substitution, N-Acetyl-Arg-Lys-Arg-$NH_2$, and derivatives thereof. Suitable pentapeptides and hexapeptides for use herein include, but are not limited to N-Palmitoyl-Lys-Thr-Thr-Lys-Ser (SEQ ID NO: 5), N-Palmitoyl-Tyr-Gly-Gly-Phe-X (SEQ ID NO: 9) with X Met or Leu or mixtures thereof, N-Palmitoyl-Val-Gly-Val-Ala-Pro-Gly (SEQ ID NO: 10) and derivatives thereof. A preferred dipeptide derivative is N-Acetyl-Tyr-Arg-hexadecylester (CALMOSENSINE® from SEDERMA, France). Preferred tripeptides and derivatives thereof include N-Palmitoyl-Gly-Lys-His (Pal-GKH from SEDERMA, France), Peptide CK (Arg-Lys-Arg) and Lipospondin (N-Elaidoyl-Lys-Phe-Lys) and its conservative substitution analogs, Peptide CK+ (N-Acetyl-Arg-Lys-Arg-$NH_2$). Suitable pentapeptides for use herein also include N-Palmitoyl-Lys-Thr-Thr-Lys-Ser (SEQ ID NO: 5), available as MATRIXYL® from SEDERMA, France. Hexapeptides such as those disclosed in French Patent Appln. No. FR 0305707, filed May 12, 2003, in the name of SEDERMA may also be used.

When included in the present compositions, the additional peptides are preferably used in amounts of from about $1 \times 10^{-6}$% to about 10%, more preferably from about $1 \times 10^{-6}$% to about 0.1%, even more preferably from about $1 \times 10^{-5}$% to about 0.01%, by weight of the composition. In certain embodiments which include the peptide CARNOSINE®, the compositions preferably contain from about 0.1% to about 5%, by weight of the composition, of such peptides. In other embodiments wherein the peptide-containing composition BIOPEPTIDE CL® is included, the resulting composition preferably contains from about 0.1% to about 10%, by weight of the composition, of the BIOPEPTIDE CL®.

Anti-Oxidants/Radical Scavengers

The compositions of the present invention may include a safe and effective amount of an anti-oxidant/radical scavenger or an oxidizer/reducing agent. The anti-oxidant/radical scavenger or oxidizer/reducing agent is especially useful for providing protection against UV radiation which can cause increased scaling or texture changes in the stratum corneum and against other environmental agents which can cause skin damage. These compounds may also be useful in hair drying and other cosmetic applications.

A safe and effective amount of an anti-oxidant/radical scavenger or an oxidizer/reducing agent may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename TROLOX®), gallic acid and its alkyl esters, especially propyl gallate, uric acid and its salts and alkyl esters, sorbic acid and its salts, lipoic acid, amines (e.g., N,N-diethylhydroxylamine, aminoguanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee.

Chelators

The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage. Examples of chelating agents include EDTA, NTA, deferoxamine, hydroxamic acids and their salts, phytic acid, phytate, gluconic acid and its salts, transferrine, lactoferrin.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are deferoxamine, hydroxamic acids, gluconic acid, phytic acid, and derivatives thereof.

Flavonoids

The compositions of the present invention may optionally contain a flavonoid compound. Flavonoids are broadly disclosed in U.S. Pat. Nos. 5,686,082 and 5,686,367, both of which are herein incorporated by reference. Flavonoids suitable for use in the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. More preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and still more preferably from about 0.5% to about 5%.

Anti-Inflammatory Agents

A safe and effective amount of an anti-inflammatory agent may be added to the compositions of the present invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, fluradrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I–III, CRC Press, Boca Raton, (1985), and Anti-inflammatory Agents, Chemistry and Pharmacology, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14, 304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin and flufenamic acid are more preferred.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora,* particularly *Commiphora Mukul*), kola extract, chamomile, red clover extract, Piper methysticum extract (Kava Kava from SEDERMA, disclosed in FR 2 771 002 of Mar. 31, 2000 and WO 99/25369), *Bacopa monieri* extract (Bacocalmine from SEDERMA, disclosed in WO 99/40897 of Aug. 19, 1999) and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Anti-Cellulite Agents

The compositions of the present invention may also contain a safe and effective amount of an anti-cellulite agent. Suitable agents may include, but are not limited to, xanthine compounds (e.g., caffeine, theophylline, theobromine, and aminophylline). Especially useful are combinations with the cellulite/slimming agents called Vexel (FR 2 654 619 of Jan. 31, 1992), Coaxel (FR 2 694 195 of Jul. 30, 1992), Cyclolipase (FR 2 733 149 of Apr. 21, 1995), Pleurimincyl and Lipocare (WO 98/43607 of Oct. 8, 1998) and Unislim (FR 0306063 of May 20, 2003), all offered by SEDERMA.

Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tanning Actives

The compositions of the present invention may contain a tanning active. When present, it is preferable that the compositions contain from about 0.1% to about 20%, more preferably from about 2% to about 7%, and still more preferably from about 3% to about 6%, by weight of the composition, of dihydroxyacetone as an artificial tanning active.

Dihydroxyacetone, which is also known as DHA or 1,3-dihydroxy-2-propanone, is a white to off-white, crystalline powder. This material can be represented by the chemical formula $C_3H_6O_3$ and the following chemical structure:

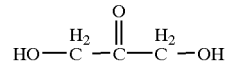

The compound can exist as a mixture of monomers and dimers, with the dimers predominanting in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See The Merck Index, Tenth Edition, entry 3167, p. 463 (1983), and "Dihydroxyacetone for Cosmetics," E. Merck Technical Bulletin, 03-304 110, 319 897, 180 588. Especially useful are combinations with the tanning agents called Tyr-ol and Tyr-exel offered by SEDERMA and described in Fr 2 702 766 of Mar. 15, 1993 and WO 03/017966 A2 of Mar. 6, 2003 respectively.

Skin Lightening Agents

The compositions of the present invention may contain a skin lightening agent. When used, the compositions preferably contain from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in the PCT publication No. 95/34280, in the name of Hillebrand, corresponding to PCT Application No. U.S. Ser. No. 95/07432, filed Jun. 12, 1995; and co-pending U.S. application Ser. No. 08/390,152 filed in the names of Kvalnes, Mitchell A. DeLong, Barton J. Bradbury, Curtis B. Motley, and John D. Carter, corresponding to PCT Publication Ser. No. 95/23780, published Sep. 8, 1995. Especially useful are combinations with the skin lightening agents called Melaclear, Etioline, Melaslow and Lumiskin offered by SEDERMA and described respectively in FR 2 732 215 of Mar. 28, 1995, WO 98/05299 of Aug. 2, 1996, WO 02/15871 of Feb. 28, 2002 and PCT/FR 03/02400 of Aug. 30, 2002.

Skin Soothing and Skin Healing Actives

The compositions of the present invention may comprise a skin soothing or skin healing active. Skin soothing or skin healing actives suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing active may be added to the present composition, preferably, from about 0.1% to about 30%, more preferably from about 0.5% to about 20%, still more preferably from about 0.5% to about 10%, by weight of the composition formed. Especially useful are combinations with the skin soothing and healing agents called Calmosensine and Bacocalmine offered by SEDERMA and described in WO 98/07744 of Feb. 26, 1998 and WO 99/40897 of Aug. 19, 1999 respectively.

Bisabolol

The topical compositions of the present invention may also contain a safe and effective amount of bisabolol. Bisabolol is a naturally occurring unsaturated monocyclic terpene alcohol having the following structure:

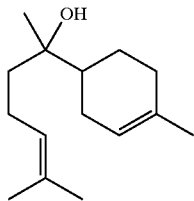

It is the primary active component of chamomile extract/oil. Bisabolol can be synthetic (d,1-alpha-isomer or (+/−)-alpha-isomer) or natural ((−)-alpha-isomer) in origin and can be used as essentially pure compounds or mixtures of compounds (e.g., extracts from natural sources such as chamomile). The alpha form of bisabolol (a-bisabolol) is used in a variety of cosmetic products as a skin conditioning or soothing agent. As used herein, "bisabolol" includes chamomile extract or oil and any isomers and tautomers of such. Suitable bisabolol compounds are commercially available as a natural material from Dragoco (Totowa, N.J.) under the product name alpha-bisabolol natural and as a synthetic material from Fluka (Milwaukee, Wis.) under the product name alpha-bisabolol. In the compositions of the present invention, the composition preferably contains from about 0.001% to about 50%, by weight of the composition, more preferably from about 0.01% to about 20%, even more preferably from about 0.01% to about 15%, and still more preferably from about 0.1% to about 10%, of bisabolol, even more preferably from about 0.1% to about 5%.

Antimicrobial and Antifungal Actives

The compositions of the present invention may contain an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and still more preferably from about 0.05% to about 2%. Especially useful are combinations with the ingredient range called OSMOCIDE offered by SEDERMA and described in WO 97/05856 of Feb. 20, 1997.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Preferred examples of actives useful herein include those selected from salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

Sunscreen Actives

Exposure to ultraviolet light can result in excessive scaling and texture changes of the stratum corneum. Therefore, the compositions of the subject invention may optionally contain a sunscreen active. As used herein, "sunscreen active" includes both sunscreen agents and physical sunblocks. Suitable sunscreen actives may be organic or inorganic.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition.

A wide variety of conventional organic sunscreen actives are suitable for use herein. Sagarin, et al., at Chapter VIII, pages 189 et seq., of Cosmetics Science and Technology (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol)(6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene boman-2-one), terephthalylidene dicamphor sulfonic acid and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

Also preferred are the compositions and combinations described and claimed in U.S. Pat. No. 6,190,645 to SaNogueira et al. and in particular, sunscreen agents disclosed at col. 3, lns. 4–23, in combination with a cinnamido alkyl amine cationic quaternary salt such as cinnamidopropyl trimethyl ammonium chloride sold under the trademark INCROQUAT-UV-283 manufactured by Croda, Inc., 7 Century Road, Parsippany, N.J. These portions of the U.S. Pat. No. 6,190,645 are herby incorporated by reference. More preferred organic sunscreen actives useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoicacid, octocrylene and mixtures thereof.

Also particularly useful in the compositions are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Especially preferred sunscreen actives include 4,4'-t-butylmethoxydibenzoylmethane, 2-ethylhexyl-p-methoxycinnamate, phenyl benzimidazole sulfonic acid, and octocrylene.

A safe and effective amount of the organic sunscreen active is used, typically from about 1% to about 20%, more typically from about 2% to about 10% by weight of the composition. Exact amounts will vary depending upon the sunscreen or sunscreens chosen and the desired Sun Protection Factor (SPF).

Particulate Material

The compositions of the present invention may contain a particulate material, preferably a metallic oxide. These particulates can be coated or uncoated, charged or uncharged. Charged particulate materials are disclosed in U.S. Pat. No. 5,997,887, to Ha et al., incorporated herein by reference. Particulate materials useful herein include: bismuth oxychloride, iron oxide, mica, mica treated with barium sulfate and TiO2, silica, nylon, polyethylene, talc, styrene, polyproylene, ethylene/acrylic acid copolymer, sericite, aluminum oxide, silicone resin, barium sulfate, calcium carbonate, cellulose acetate, titanium dioxide, polymethyl methacrylate, and mixtures thereof.

Inorganic particulate materials, e.g., TiO2, ZnO, or ZrO2 are commercially available from a number of sources. One example of a suitable particulate material contains the material available from U.S. Cosmetics (TRONOX TiO2 series, SAT-T CR837, a rutile TiO2). Preferably, particulate materials are present in the composition in levels of from about 0.01% to about 2%, more preferably from about 0.05% to about 1.5%, still more preferably from about 0.1% to about 1%, by weight of the composition.

Conditioning Agents

The compositions of the present invention may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al., issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360, to Volpenhein, issued May 21, 1985.

Preferably, the conditioning agent is selected from urea, guanidine, sucrose polyester, panthenol, dexpanthenol, allantoin, and combinations thereof.

Structuring Agents

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention contain from about 0.1% to about 20%, more preferably from about 0.1% to about 10%, still more preferably from about 0.5% to about 9%, of one or more structuring agents.

Preferred structuring agents are those having an HLB of from about 1 to about 8 and having a melting point of at least about 45° C. Suitable structuring agents are those selected from saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present invention are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

Thickening Agent (Including Thickeners and Gelling Agents)

The compositions of the present invention can contain one or more thickening agents, preferably from about 0.1% to about 5%, more preferably from about 0.1% to about 4%, and still more preferably from about 0.25% to about 3%, by weight of the composition.

Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; and in CTFA International Cosmetic Ingredient Dictionary, Ninth Edition, 2002.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Godrich) and copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10}$–$C_{30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/$C_{10}$–$C_{30}$ alkyl acrylate crosspolymers, and mixtures thereof.

b) Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987.

c) Polyacrylamide Polymers

The compositions of the present invention can optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc. (Paterson, N.J.).

Ready-Made Gels

The compositions may also contain thickening and texturising gels of the type as exemplified by the product range called Lubrajel® from United Guardian, 230 Marcus Blvd, Hauppauge N.Y. 11788. These gels have moisturizing, viscosifying, stabilizing properties and may be used in concentration ranges between 1 and 99%, most advantageously between 5 and 15%.

d) Polysaccharides

A wide variety of polysaccharides are useful herein. "Polysaccharides" refer to gelling agents which contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkyl-celluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans which are a linear chain of (1–3) linked glucose units with a (1–6) linked glucose every three units, a commercially available example of which is Clearogel™ CS11 from Michel Mercier Products Inc. (Mountainside, N.J.).

e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Preferred compositions of the present invention include a thickening agent selected from carboxylic acid polymers, crosslinked polyacrylate polymers, polyacrylamide polymers, and mixtures thereof, more preferably selected from carboxylic acid polymers, polyacrylamide polymers, and mixtures thereof.

Dermatologically-Acceptable Carrier

The compositions of the invention may be used in various cosmetic and/or personal care products, for example, skin care, hair care, nail care, facial and body care and sunscreen compositions, such as lotions, gels, sprays, and the like, hand cleaners, bath compositions, suntan oils, antiperspirant compositions, perfumes and colognes, cold creams, hair sunscreen compositions, pre-shaves, deodorants, topical pharmaceutical ointments, skin moisturizers, facial cleansers, cleansing creams, skin gels, shampoos, hair conditioners, detergents, household cleaning products, make-up products, lipstick products, mascara, and hair coloring products. Therefore, in addition to any of the above cited skin care or hair care peptides and other actives, the cosmetic compositions described in the present invention may often include as an additional ingredient a dermatologically acceptable carrier. The form of the carrier and the final product resulting from the combination of the tetrapeptides with any additional active and with the carrier may be any of the following: liquids, gels, creams, water-in-oil and oil-in-water, and silicone emulsions, foams, and solids; they may be clear or opaque; and may be formulated as both aqueous and non-aqueous preparations, including but not limited to topical preparations.

To realize the invention in any of these physical forms, further substances, agents and compounds are useful although not always necessary such as Conditioning Agents, Structuring Agents and Thickening Agents. These compounds sometimes also have the role of adjuvant and sometimes the role of additional ingredient. Neither role excludes them from the present invention as being combined with the tetrapeptide/tripeptide mixtures of the invention and their derivatives.

The nature of the dermatologically acceptable carrier, the nature of the final product, and the methods of preparing those need not be described here in detail; many examples can be found in the available literatures, such as PCT application No. WO 00/62743 filed by Larry R. Robinson et al. on Apr. 19, 2000, published on Oct. 26, 2000, or, more generally, in Milady's *Standard Textbook of Cosmetology 2000*, (Delmar Learning) or in *Formulation Technology: Emulsions, Suspensions, Solid Forms* by Hans Mollet, Arnold Grubenmann and Helen Payne, published by John Wiley & Sons (Jan. 23, 2001), or in *Chemistry and Technology of the Cosmetics and Toiletries Industry* by Clifford Williams Schmitt, Kluwer Academic Publishers, Dordrecht July 1996, all hereby incorporated. Fiedler's *Encyclopedia of Excipients*, fifth edition, Edition Cantor Verlag Aulendorf, 2002 is also a useful guide for the formulator skilled in the art of developing cosmetic carriers. All ingredients listed therein may in one way or another be combined to form a dermatologically acceptable carrier and/or used as an additional ingredient for the cosmetic compositions of the invention.

In most instances, the additional ingredients will include a dermatologically acceptable carrier either alone or in combination with still other additional ingredients. The amounts of additional ingredients may range from about 99.5% to about 99.99999%, preferably from about 99.9% to about 99.9999%, more preferably from about 99.99% to about 99.999%, of the composition. In short, it is the balance of the composition. If carriers (either singularly, such as water, or complex cosolvents) are used, they may make up the entire balance of the compositions.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers contain an emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition. Oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317–324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, still more preferably about 5 centistokes or less.

Preferred water-in-silicone and oil-in-water emulsions are described in greater detail below.

A) Water-in-Silicone Emulsion

Water-in-silicone emulsions contain a continuous silicone phase and a dispersed aqueous phase.

(1) Continuous Silicone Phase

Preferred water-in-silicone emulsions of the present invention contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the retinoid. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in PCT Application WO 97/21423, published Jun. 19, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and still more preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

(2) Dispersed Aqueous Phase

The topical compositions of the present invention contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelants, gums, water-soluble or dispersible alcohols and polyols, buffers, preservatives, sunscreening agents, colorings, and the like.

The topical compositions of the present invention will typically contain from about 25% to about 90%, preferably from about 40% to about 80%, more preferably from about 60% to about 80%, water in the dispersed aqueous phase by weight of the composition.

(3) Emulsifier for Dispersing the Aqueous Phase

The water-in-silicone emulsions of the present invention preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present invention, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$–$C_{30}$ pendant side chains. Still other useful dimethicone copolyols include materials having various cationic, anionic, amphoteric, and zwitterionic pendant moieties.

The dimethicone copolyol emulsifiers useful herein can be described by the following general structure:

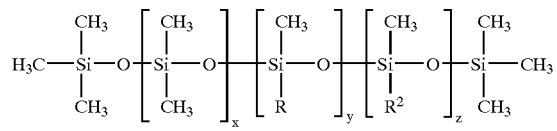

wherein R is $C_1$–$C_{30}$ straight, branched, or cyclic alkyl and $R^2$ is selected from the group consisting of:

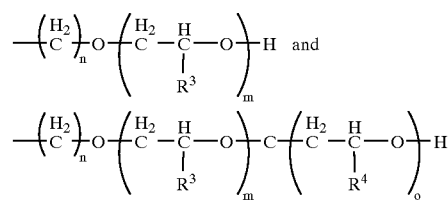

wherein n is an integer from 3 to about 10; $R^3$ and $R^4$ are selected from the group consisting of H and $C_1$–$C_6$ straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is: —$(CH_2)_n$—O—$R^5$, wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See International Cosmetic Ingredient Dictionary, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to SanoGueira, published Aug. 30, 1989; G. H. Dahms, et al., "New Formulation Possibilities Offered by Silicone Copolyols," Cosmetics & Toiletries, vol. 110, pp. 91–100, March 1995; M. E. Carlotti et al., "Optimization of W/O-S Emulsions And Study Of The Quantitative Relationships Between Ester Structure And Emulsion Properties," J. Dispersion Science And Technology, 13(3), pp. 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," Provisional Communication International Journal of Cosmetic Science, 12, pp. 135–139 (1990); and D. G. Krzysik et al., "A New Silicone Emulsifier For Water-in-Oil Systems," Drug and Cosmetic Industry, vol. 146(4) pp. 28–81 (April 1990).

Among the non-silicone-containing emulsifiers useful herein are various non-ionic and anionic emulsifying agents such as sugar esters and polyesters, alkoxylated sugar esters and polyesters, $C_1$–$C_{30}$ fatty acid esters of $C_1$–$C_{30}$ fatty alcohols, alkoxylated derivatives of $C_1$–$C_{30}$ fatty acid esters of $C_1$–$C_{30}$ fatty alcohols, alkoxylated ethers of $C_1$–$C_{30}$ fatty alcohols, polyglyceryl esters of $C_1$–$C_{30}$ fatty acids, $C_1$–$C_{30}$ esters of polyols, $C_1$–$C_{30}$ ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

B) Oil-in-Water Emulsions

Other preferred topical carriers include oil-in-water emulsions, having a continuous aqueous phase and a hydrophobic, water-insoluble phase ("oil phase") dispersed therein. Examples of suitable oil-in-water emulsion carriers are described in U.S. Pat. No. 5,073,371, to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

(1) Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention contain from about 0.5% to about 20%, more preferably from about 1% to about 10%, even more preferably from about 1% to about 5%, by weight of the composition, of a structuring agent.

The preferred structuring agents of the present invention include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

(2) Hydrophilic Surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from nonionic surfactants. Among the nonionic surfactants that are useful herein are those that can be broadly defined as condensation products of long chain alcohols, e.g. $C_8$–$C_{30}$ alcohols, with sugar or starch polymers, i.e., glycosides. These compounds can be represented by the formula $(S)_n$—

O—R wherein S is a sugar moiety such as glucose, fructose, mannose, and galactose; n is an integer of from about 1 to about 1000, and R is a $C_8$–$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_8$–$C_{20}$ alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a $C_{10}$–$C_{30}$ alkyl group, X is —$OCH_2CH_2$— (i.e. derived from ethylene glycol or oxide) or —$OCH_2CH(CH_3)$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a $C_{10}$–$C_{30}$ alkyl group, X is —$OCH_2CH_2$— (i.e. derived from ethylene glycol or oxide) or —$OCH_2CH(CH_3)$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_nOR'$ wherein R is a $C_{10}$–$C_{30}$ alkyl group, X is —$OCH_2CH_2$— (i.e., derived from ethylene glycol or oxide) or —$OCH_2CH(CH_3)$— (i.e., derived from propylene glycol or oxide), and n is an integer from about 6 to about 100 and R' is H or a $C_{10}$–$C_{30}$ alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are $C_{10}$–$C_{30}$ alkyl groups, X is —$OCH_2CH_2$— (i.e., derived from ethylene glycol or oxide) or —$OCH_2CH(CH_3)$— (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809, 060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, $C_1$–$C_{30}$ fatty acid esters of $C_1$–$C_{30}$ fatty alcohols, alkoxylated derivatives of $C_1$–$C_{30}$ fatty acid esters of $C_1$–$C_{30}$ fatty alcohols, alkoxylated ethers of $C_1$–$C_{30}$ fatty alcohols, polyglyceryl esters of $C_1$–$C_{30}$ fatty acids, $C_1$–$C_{30}$ esters of polyols, $C_1$–$C_{30}$ ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably $C_8$–$C_{24}$, more preferably $C_{10}$–$C_{20}$. The preferred fatty acid ester emulsifier is a blend of sorbitan or sorbitol $C_{16}$–$C_{20}$ fatty acid ester with sucrose $C_{10}$–$C_{16}$ fatty acid ester, especially sorbitan stearate and sucrose cocoate. This is commercially available from ICI under the trade name Arlatone 2121.

Other suitable surfactants useful herein include a wide variety of cationic, anionic, zwitterionic, and amphoteric surfactants such as are known in the art and discussed more fully below. See, e.g., McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds or "quats", examples of which are described in U.S. Pat. No. 5,151,209; U.S. Pat. No. 5,151,210; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's Detergents & Emulsifiers, (North American edition 1979) M.C. Publishing Co.; and Schwartz, et al., Surface Active Agents, Their Chemistry and Technology, New York: Interscience Publishers, 1949; which descriptions are incorporated herein by reference. The cationic surfactants useful herein include cationic ammonium salts such as those having the formula:

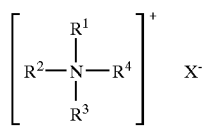

wherein $R_1$, is an alkyl group having from about 12 to about 30 carbon atoms, or an aromatic, aryl or alkaryl group having from about 12 to about 30 carbon atoms; $R^2$, $R^3$, and $R^4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Still more preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5$CONH—$(CH_2)_n$, wherein $R_5$ is an alkyl group having from about 12 to about 22 carbon atoms, and n is an integer from about 2 to about 6, more preferably from about 2 to about 4, and still more preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO-OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1-SO_3-M$$

wherein $R_1$ is chosen from the group including a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8-C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_mCO_2M]_2$ and $RNH(CH_2)_mCO_2M$ wherein m is from 1 to 4, R is a $C_8-C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Other amphoteric or zwitterionic surfactants useful herein include betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

When the surfactant used is a quaternary nitrogen containing compound ("quat") or indeed when a quat material is used in compositions or products in accordance with preferred embodiments of the invention, cationic activity may be used as a measure of the amount of quat actually used.

Cationic activity is appropriate for discussion in the context of quats. Cationic activity may be measured by several methods readily understood by those skilled in the art. One such method utilizes a standardized solution of an anionic material, such as sodium lauryl sulfate. This material is added to the solution containing the quat until full complexation of the quat's cations (the end point) has been reached. The end point can be measured potentiometrically or by the use of color indicators.

Typical tests involve titrating a sample of the quat, usually dissolved in a solvent, with the standardized solution of sodium lauryl sulfate until the endpoint is reached. As described in the co-pending and co-assigned U.S. patent application Ser. No. 09/438,631, incorporated by reference herein in its entirety, once the endpoint is reached, the cationic activity can be calculated according to the following formula:

$$\% \text{ cationic activity} = \frac{mL \times N \times MW \times 100}{S.wt. \times 1000}$$

Where:
mL=the number of mL of anionic material
N=the normality of the solution used
MW=the equivalent molecular weight of the quat being analyzed
S.wt.=the sample weight in grams
For additional information regarding the methodology for measuring the cationic activity, see W. Schempp and H. T.

Trau, *Wochenblatt fur Papierfabrikation* 19, 1981, pages 726–732, or J. P. Fischer and K. Lohr, *Organic Coatings Science Technology*, Volume 8, pages 227–249, Marcel Dekker, Inc. April 1986), both incorporated herein by reference in their entirety. While the use of quat raw materials having a high cationic activity is preferred (activity of at least about 35%, more preferably at least about 50%), use of lower cationic activities are also contemplated, particularly in finished products where the overall cationic activity may be less than 25%, less than 10% and even less than 5%.

(3) Water

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients are known and may be used herein. Sagarin, Cosmetics Science and Technology, 2nd Edition, Vol. 1, pp. 32–43 (1972), incorporated herein by reference, contains numerous examples of materials suitable as an emollient. A preferred emollient is glycerin. Glycerin is preferably used in an amount of from or about 0.001 to or about 30%, more preferably from or about 0.01 to or about 20%, still more preferably from or about 0.1 to or about 10%, e.g., 5%.

Examples of suitable emollients include $C_8$–$C_{30}$ alkyl esters of $C_8$–$C_{30}$ carboxylic acids; $C_1$–$C_6$ diol monoesters and diesters of $C_8$–$C_{30}$ carboxylic acids; monoglycerides, diglycerides, and triglycerides of $C_8$–$C_{30}$ carboxylic acids, cholesterol esters of $C_8$–$C_{30}$ carboxylic acids, cholesterol, and hydrocarbons. Examples of these materials include diisopropyl adipate, isopropyl myristate, isopropyl palmitate, ethylhexyl palmitate, isodecyl neopentanoate, $C_{12-15}$ alcohols benzoates, diethylhexyl maleate, PPG-14 butyl ether, PPG-2 myristyl ether propionate, cetyl ricinoleate, cholesterol stearate, cholesterol isostearate, cholesterol acetate, jojoba oil, cocoa butter, shea butter, lanolin, lanolin esters, mineral oil, petrolatum, and straight and branched $C_{16}$–$C_{30}$ hydrocarbons.

Also useful are straight and branched chain fatty $C_8$–$C_{30}$ alcohols, for example, stearyl alcohol, isostearyl alcohol, ethenyl alcohol, cetyl alcohol, isocetyl alcohol, and mixtures thereof. Examples of other suitable emollients are disclosed in U.S. Pat. No. 4,919,934; which is incorporated herein by reference in its entirety.

Other suitable emollients are various alkoxylated ethers, diethers, esters, diesters, and trimesters. Examples of suitable alkoxylated ethers include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Examples of alkoxylated diethers include PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof.

Examples of suitable alkoxylated diesters and trimesters are disclosed in U.S. Pat. Nos. 5,382,377, 5,455,025 and 5,597,555, assigned to Croda Inc., and incorporated herein by reference.

Suitable lipids include $C_8$–$C_{20}$ alcohol monosorbitan esters, $C_8$–$C_{20}$ alcohol sorbitan diesters, $C_8$–$C_{20}$ alcohol sorbitan triesters, $C_8$–$C_{20}$ alcohol sucrose monoesters, $C_8$–$C_{20}$ alcohol sucrose diesters, $C_8$–$C_{20}$ alcohol sucrose triesters, and $C_8$–$C_{20}$ fatty alcohol esters of $C_2$–$C_{62}$-hydroxy acids. Examples of specific suitable lipids are sorbitan diisostearate, sorbitan dioleate, sorbitan distearate, sorbitan isostearate, sorbitan laurate, sorbitan oleate, sorbitan palmitate, sorbitan sesquioleate, sorbitan sesquistearate, sorbitan stearate, sorbitan triisostearate, sorbitan trioleate, orbitan tristearate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof.

Other suitable emollients include mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearate, sorbitan dilaurate, sorbitan stearate, sorbitan laurate, sucrose laurate, sucrose dilaurate, sodium isostearyl lactylate, lauryl pidolate, PPG-14 butyl ether, PPG-15 stearyl ether, and mixtures thereof.

Lotions and creams according to the present invention generally contain a solution carrier system and one or more emollients. Lotions and creams typically contain from about 1% to about 50%, preferably from about 1% to about 20%, of emollient; from about 50% to about 90%, preferably from about 60% to about 80% of water; and the tetrapeptide and tripeptide mixture and the optional additional skin care active (or actives) in the above described amounts. Creams are generally thicker than lotions due to higher levels of emollients or higher levels of thickeners.

Ointments of the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, Cosmetics, Science and Technology, 2nd Edition, Vol. 1, pp. 72–73 (1972), incorporated herein by reference, and/or an emollient. For example, an ointment may contain from about 2% to about 10% of an emollient; from about 0.1% to about 2% of a thickening agent; and the tetrapeptide and tripeptide mixture and the optional additional skin care active (or actives) in the above described amounts.

Compositions of this invention useful for cleansing ("cleansers") are formulated with a suitable carrier, e.g., as described above, and preferably contain, in addition to the tetrapeptide and tripeptide mixture and the optional additional skin care active (or actives) in the above described amounts, from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in McCutcheon's Detergents and Emulsifiers, North American Edition (1986), published by Allured Publishing Corporation. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier and may include conventional ingredients such as oils, colorants, pigments, emollients, fragrances, waxes, stabilizers, and the like. Exemplary carriers and such other ingredients which are suitable for use herein are described, for example, in PCT Application, WO 96/33689, to Canter, et al., published on Oct. 31, 1996 and U.K. Patent, GB 2274585, issued on Aug. 3, 1994.

A preferred embodiment contains the tetrapeptide Gly-Gln-Pro-Arg (SEQ ID NO: 3), its analogs and its N-Acyl-derivatives, the tripeptide Gly-His-Lys, its analogs and its N-Acyl-derivatives, and a dermatologically acceptable carrier. And particularly, the composition can contain the N-acyl-tetrapeptide N-palmitoyl-Gly-Gln-Pro-Arg (SEQ ID NO: 3), the N-acyl-tripeptide N-palmitoyl-Gly-His-Lys, and a dermatologically acceptable carrier.

When included in the present compositions, the additional peptides are preferably included in amounts from about 0.1 ppm (0.00001%) to about 5,000 ppm (0.5%), preferably from about 1 ppm to about 100 ppm (0.01%), by weight of the composition.

The compositions of the invention may also include a hair setting agent to impart styling benefits upon application to hair. The hair setting polymers may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic.

Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyltriethylammonium bromide; amine derivatives of methacrylic acid or amine derivatives of methacrylamide derived from methacrylic acid or methacrylamide and a dialkylalkanolamine having $C_1$–$C_6$ alkyl groups such as dimethylaminoethyl(meth)acrylate, diethylaminoethyl(meth)acrylate, dimethylaminopropyl (meth)acrylate, or dimethylaminopropyl(meth)acrylamide.

Examples of the amphoteric monomers include zwitterionized derivatives of the aforementioned amine derivatives of (meth)acrylic acids or the amine derivatives of (meth)acrylamide such as dimethylaminoethyl(meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

Examples of nonionic monomers are acrylic or methacrylic acid esters of $C_1$–$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene, chlorostyrene, vinyl esters such as vinyl acetate, vinyl chloride, vinylidene chloride, acrylonitrile, alpha-methylstyrene, t-butylstyrene, butadiene, cyclohexadiene, ethylene, propylene, vinyl toluene, alkoxyalkyl(meth)acrylate, methoxy ethyl(meth)acrylate, butoxyethyl(meth)acrylate, allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl(meth)acrylate, n-butyl methacrylate, isobutyl methacrylate, 2-ethylhexyl methacrylate, methyl methacrylate, t-butylacrylate, t-butylmethacrylate, and mixtures thereof.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

The compositions of the invention may also include a wide range of miscellaneous ingredients. Some suitable miscellaneous ingredients commonly used in the cosmetic and personal care industry are described in *The CTFA Cosmetic Ingredient Handbook*, (9$^{th}$ Ed., 2002), which is incorporated by reference herein. These ingredients will be used in amounts which are conventional.

Compositions

The physical form of the compositions according to the invention is not important: creams, lotions, ointments, gels, emulsions, dispersions, solutions, suspensions, cleansers, foundations, anhydrous preparations (sticks, in particular lipsticks, body and bath oils), shower and bath gels and washes, shampoos and scalp treatment lotions, skin "essences," serums, adhesive or absorbent materials, transdermal patches, and powders can all incorporate the tetrapeptide/tripetide mixtures, their analogs and derivatives thereof as well as combinations of these compounds with other additional ingredients.

The present invention also contemplates various uses. First, the invention contemplates the use of a mixture of tetrapeptides and tripeptides in cosmetics or personal care products and their use for cosmetic and personal care purposes. In particular, products produced in accordance with the present invention can be used to help mitigate the visible signs of aging, which include all outwardly visible and tactily perceptible manifestations as well as other macro or micro effects due to skin aging. Such signs may be induced or caused by intrinsic or extrinsic factors. The use in reducing these signs may be general or may be specific to use in reducing the visible signs of development of textural discontinuities, skin lines, crevices, bumps, large pores or skin unevenness or roughness, loss of skin elasticity, sagging, loss of skin firmness, loss of skin tightness, loss of skin recoil from deformation, discoloration, blotching, sallowness, hyperpigmented skin regions, keratoses, abnormal differentiation, hyperkeratinisation, elastosis, collagen breakdown, stretch marks, dark circles and the like. The use of these formulations for these cosmetic purposes may produce some extended change in the skin, but often produces a more transitory reduction in the visible manifestations of various conditions.

The present invention can also be used to manufacture a medicament capable of prophylatically or therapeutically regulating a skin condition including signs of aging, dark circles and stretch marks. This includes delaying, minimizing or preventing visible or tactile discontinuities. Often, but not exclusively, these are part of some longer term therapeutic application, rather than a merely cosmetic or personal care application.

The skin care compositions therefore can be used to make a medicament for reducing the visible signs of aging of human skin, reducing wrinkles and/or increasing collagen I synthesis compared to normal levels of a patient (prior to application of the invention) by topical application of said medicament to the skin of the human needing such treatment.

Methods for Improving Skin Condition

The compositions of the present invention are useful for preventing and/or reducing the visible signs of aging, and for improving the state of human skin or hair and its appearance. This includes preventive and curative treatment of the skin. For example, such methods are intended to thicken the various skin layers and tissues, preventing the thinning of the skin, preventing and/or retarding the appearance of wrinkles, improving firmness and elasticity of the skin, softening and/or smoothing lips, hair and nails, preventing and/or relieving itch, diminishing wrinkles and fine lines, diminishing stretch marks and dark circles, and/or stimulate collagen I synthesis.

This method of improving skin appearance involves topically applying to the skin or hair an effective amount of a composition of the present invention. The amount of the composition which is needed, the frequency of application and the duration period of use will depend on the amount of tetrapeptide/tripeptides, analogs or derivatives thereof contained in the composition and on the specific combination with other additional ingredients, which can include, for example, pharmaceutically active agents, vitamins, alphahydroxy acids and the like, and the strength of the cosmetic effect desired.

Most advantageously, the compositions of the invention are applied to the skin or hair, once or twice a day, over an extended period of time, at least one week, preferably one month, even more preferably 3 months, even more preferably for at least about six months, and more preferably still for at least about one year.

Amounts of the composition and products applied to the skin are, per application, preferably in the range of about 0.1 mg/cm$^2$ to about 10 mg/cm$^2$.

To practice the method, a composition in the form of a skin lotion, cream, gel, foam, ointment, paste, emulsion, spray, conditioner, tonic, cosmetic make-up, lipstick, foundation, nail polish, after-shave or the like, is applied to the skin and intended to stay there (leave-on). The composition can be applied manually, with the aid of spatulas, wipes or similar cosmetic tools. It can also be applied by the use of an occlusive or semi-occlusive patch, an adhesive or non-adhesive tissue.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

Anti-Wrinkle Night Cream

| PRODUCT | INCI name | % |
|---|---|---|
| I. PHASE A | | |
| H$_2$O | | 70.95 |
| Ultrez 10 | Carbomer | 0.15 |
| PHASE B | | |
| Glycerine | Glycerin | 3.50 |

-continued

| PRODUCT | INCI name | % |
|---|---|---|
| PHASE C | | |
| Volpo S 2 | Steareth 2 | 0.40 |
| Crodafos CES | Cetearyl alcohol dicetyl phosphate & ceteth 10 phosphate | 4.00 |
| DC 345 | Cyclohexasiloxane | 2.00 |
| Crodamol OSU | Dioctyl succinate | 7.00 |
| Volpo S 10 | Steareth 10 | 1.20 |
| Nipastat | Mixed parabens | 0.30 |
| PHASE D | | |
| Sorbate | Sorbate | 0.10 |
| PHASE E | | |
| H$_2$O | | 2.50 |
| N$_a$OH 38% | Sodium hydroxyde | 0.30 |
| PHASE F | | |
| II. Perfume | Fragrance | 0.10 |
| PHASE G | | |
| MATRIXYL ® 3000 | *) | 3.00 |

*)MATRIXYL 3000 ® is sold by SEDERMA, 29 rue du chemin vert- BP 33, 78612 Le Perray-en-Yvelines cedex France and contains: butylene glycol, carbomer, polysorbate-20, N-Palmitoyl-Gly-Gln-Pro-Arg (SEQ ID NO: 3) and N-Palmitoyl-Gly-His-Lys. The concentration of the tetrapeptide is 0.005% (w/w) and the concentration of the tripeptide is 0.01%, thus in the example cited, the amount of tripeptide is 0.0003% and of tetrapeptide 0.00015%.

This emulsion is prepared in the following way: Phase A: disperse Ultrez 10 in water and let it swell for 20 minutes, then add phase B; heat to 75° C. Heat Phase C separately to 75° C.
Mix the two phases under stirring, homogenise, add Phase D, neutralise with Phase E, cool until reaching 30° C., then add Phase F and Phase G, adjust pH to ~6 with NaOH.
The resulting emulsion should be well suited for fragile, aged skin, to improve fine lines, wrinkles, and dryness, reduce redness and irritation.

Example 2

Decrease in the Wrinkles Around the Eyes (In Vivo)

Fifteen female elderly volunteers with wrinkles around their eyes took part in a study on the use of a cream as per Example No. 1.

The wrinkles around the eyes were assayed by self-evaluation via a questionnaire and by the standard skin replica method. Briefly, this consists in applying a polymer to the eyezone which, when hardened, can be peeled off to reveal a "negative" profile of the skin surface. Instrumental profilometry then measures wrinkle depth, length, volume etc. The cream product of Example No. 1 was then applied by the panelists to the target areas twice daily for 56 days to one eye and a control without the peptides was applied to the other eye of each subject. The amount applied varied from subject to subject. However, the amounts used were consistent from eye to eye. The replica determinations were conducted on day 0 and day 56. The results showed a measurable decrease in the wrinkles of up to 60% of their depth in the eyezone to which the formulation of Example 1 was applied. Moreover, the decrease could be observed with the naked eye while the sites treated with the same cream devoid of peptides showed no significant improvement in the symptoms of cutaneous aging.

Example 3

Increase in Synthesis of Collagen (In Vitro)

Fibroblasts of human skin are incubated for 72 hours in two culture mediums enriched in vitamin C (1.5 and 15 ppm), in the presence of the peptide N-palmitoyl-Gly-Gln-Pro-Arg (SEQ ID NO: 3) at two different concentrations, 2.5 ppm and 3.6 ppm. After this incubation, the media is collected and cell viability is evaluated by MTT assay. The measurement of collagen is then carried out by ELISA in each cell lysate. Tests were done in triplicate.

In parallel, negative controls should be carried out under the same conditions, but in the absence of the peptides.

The following results, shown in Table 2, give the increase of collagen synthesis compared to the results obtained in the blank tests (without peptide):

TABLE 2

| | N-palmitoyl-Gly-Gln-Pro-Arg (SEQ ID NO: 3) concentrations | |
|---|---|---|
| Vitamin C | 2.5 ppm | 3.6 ppm |
| 1.5 ppm | +10% | +29% |
| 15 ppm | +27% | +42% |

Example 4

Anti-Wrinkle Cream with Skin Whitening Activity

| Ingredients | | % by wt |
|---|---|---|
| Water Deionised | — | qs 100 |
| Carbomer | — | 0.10 |
| Potassium Sorbate | — | 0.10 |
| Transcutol | — | 3.00 |
| Glycerin | Croda | 8.00 |
| Volpo S2 [Steareth 2] | Croda | 0.60 |
| Crodafos CES [Cetearyl Alcohol (and) Dicetyl Phosphate (and) Ceteth 10 Phosphate] | Croda | 4.00 |
| DC 344 [Cyclomethicone] | Dow Corning | 2.00 |
| Crodamol GTCC [Caprylic/Capric Triglyceride] | Croda | 10.00 |
| Crill 3 [Sorbitan Stearate] | Croda | 1.60 |
| Mixed Parabens | — | 0.30 |
| Sodium Hydroxide 30% | — | 0.35 |
| Water Deionised | — | 3.50 |
| MATRIXYL 3000 ® | Sederma | 3.00 |
| ETIOLINE ® [Glycerine (and) Butylene Glycol (and) Arcostaphylus uva leaf extract and Mitracarpus Scaber extract] *) | Sederma | 3.00 |

*) ETIOLINE ® is a skin lightening ingredient sold by SEDERMA (WO 98/05299 of Nov. 19, 1996). This formulation can be made according to the procedures generally outlined in Example 1.

Example 5

Anti Stretch-Mark Cream

| Ingredients | | % by wt |
|---|---|---|
| Part A | | |
| Water Deionised | — | qs 100 |
| Ultrez 10 [Carbomer] | Noveon | 0.40 |
| Part B | | |
| Glycerin | Croda | 5.00 |
| Phenova [Phenoxyethanol (and) Mixed Parabens] | Crodarom | 0.80 |
| Part C | | |
| Crodamol OP [Ethylhexyl Palmitate] | Croda | 4.00 |
| Crodacol CS90 [Cetearyl alcohol] | Croda | 0.50 |
| Crodamol ML [Myristyl Lactate] | Croda | 0.30 |
| Crillet 1 [Polysorbate 20] | Croda | 1.00 |
| Part D | | |
| Pemulen TR2 [Acrylates/C 10–30 Alkyl Acrylate (and) Crosspolymer] | Noveon | 0.20 |
| DC 345 [Cyclomethicone] | Dow Corning | 2.00 |
| Part E | | |
| Potassium Sorbate | — | 0.10 |
| Part F | | |
| Water | — | 6.00 |
| Sodium Hydroxide 38% | — | 0.60 |
| Part G | | |
| MATRIXYL ® 3000 | SEDERMA | 3.00 |
| Darutoside (Siegesbeckia Orientalis Extract) | SEDERMA | 2.00 |

Darutoside is a molecule sold by SEDERMA for the treatment of stretch marks.

This emulsion is prepared in the following way: Phase A disperse Ultrez 10 in water and let it swell for 20 minutes, then add phase B; heat to 75° C. Heat Phase C separately to 75° C. Mix the two phases under stirring, homogenise, add Phase D, neutralise with Phase E, cool until reaching 30° C., then add Phase F and Phase G, adjust pH to ~6 with NaOH.

Example 6

Moisturising Face Gel

| Ingredients | | % by wt |
|---|---|---|
| Part A | | |
| Ultrez 10 [Carbomer] | Noveon | 0.20 |
| Water Deionised | — | qs 100 |
| Part B | | |
| Glycerin | Croda | 3.00 |
| Phenova [Phenoxyethanol (and) Mixed Parabens] | Crodarom | 0.80 |
| Part C | | |
| Crillet 1 [Polysorbate 20] | Croda | 0.50 |
| Part D | | |
| Potassium Sorbate | — | 0.10 |
| Part E | | |
| Pemulen TR1 [Acrylates/C10–30 Alkyl Acrylate Crosspolymer] | Noveon | 0.20 |
| DC 345 [Cyclomethicone] | Dow Corning | 3.00 |
| Part F | | |
| Water | — | 4.00 |
| Sodium Hydroxide 38% | — | 0.40 |
| Part G | | |
| MATRIXYL ® 3000 | SEDERMA | 3.00 |
| MOIST-24 ® [Imperata Cylindrica (root) Extract (and) water (and) Glycerin (and) PEG-8 (and) Carbomer] | SEDERMA | 5.00 |

MOIST-24 is a moisturising plant extract sold by SEDERMA (WO 01/62218 of Aug. 30, 2001). This formulation can be made according to the procedures generally outlined in Example 5.

Example 7

Anti-Age Soothing Day Cream

| Ingredients | | % by wt |
|---|---|---|
| Part A | | |
| Water Deionised | — | qs 100 |
| Ultrez 10 [Carbomer] | Noveon | 0.20 |
| Part B | | |
| Potassium Sorbate | — | 0.10 |
| Part C | | |
| Butylene Glycol | — | 2.00 |
| Phenova [Phenoxyethanol (and) Mixed Parabens] | Crodarom | 0.80 |
| Part D | | |
| Crill 3 [Sorbitan Stearate] | Croda | 1.00 |
| Crillet 3 [Polysorbate 60] | Croda | 2.50 |
| DC 200 [Dimethicone] | Dow Corning | 2.50 |
| Crodamol TN [Isotridetyl Isononanoate] | Croda | 5.00 |
| Crodamol GTCC [Caprylic/Capric Triglyceride] | Croda | 5.00 |
| Crodamol SS [Cetyl Esters] | Croda | 1.00 |
| Super Hartolan [Lanolin Alcohol] | Croda | 0.50 |
| Super Sterol Ester [$C_{10}$–$C_{30}$ Cholesterol/Lanosterol esters] | | 0.30 |
| Crodacol CS90 [Cetearyl Alcohol] | Croda | 3.00 |
| Part E | | |
| Water Deionised | — | 2.50 |
| Sodium Hydroxide 38% | — | 0.25 |
| Part F | | |
| MATRIXYL ® 3000 | SEDERMA | 3.00 |
| CALMOSENSINE ® [Butylene Glycol (and) water (and) Laureth-3 (and) Hydroxyethylcellulose (and) Acetyl-Dipeptide-1-cetylester] | SEDERMA | 4.00 |

Calmosensine® is an analgesic peptide offered by SEDERMA (WO 98/07744 of Feb. 26, 1998).

This formulation can be made according to the procedures generally outlined in Example 5.

Example 8

Cream for Mature Skin with Isoflavones

| Ingredients | | % by wt. |
|---|---|---|
| Part A | | |
| Ultrez 10 [Carbomer] | Noveon | 0.20 |
| Water Deionised | — | qs 100 |
| Part B | | |
| Glycerin | — | 3.50 |
| Part C | | |
| Potassium Sorbate | — | 0.10 |
| Part D | | |
| Volpo S10 [Steareth 10] | Croda | 1.50 |
| Crodafos CES [Ceterayl Alcohol Dicetyl Phosphate (and) Ceteth-10 Phosphate] | Croda | 3.50 |
| DC 200 [Dimethicone] | Dow Corning | 2.00 |
| Crodamol OSU [Diethylhexyl Succinate] | Croda | 7.00 |
| Mixed Parabens | — | 0.30 |
| Crill 3 [Sorbitan Stearate] | Croda | 0.40 |
| Part E | | |
| Sodium Hydroxide 38% | — | 0.20 |
| Water Deionised | — | 4.00 |
| Part F | | |
| STEROCARE ™ [Trifolium Pratense (Clover) Flower Extract (and) Glycerin (and) Butylene Glycol (and) Lecithin] | SEDERMA | 3.00 |
| MATRIXYL 3000 ® | SEDERMA | 3.00 |

Sterocare® is offered by SEDERMA as an active ingredient for mature skin (FR 2769502 of Apr. 14, 2000, WO 99/18927 of Apr. 22, 1999). This formulation can be made according to the procedures generally outlined in Example 5.

Example 9

Hair Tonic Against Hair Loss

| Ingredients | | % by wt |
|---|---|---|
| Part A | | |
| Water deionised | — | Qs 100 |
| Part B | | |
| Mixed Parabens | — | 0.14 |
| Butylene Glycol | — | 2.00 |
| Part C | | |
| Pal-Gly-His-Lys | | 0.0005 |
| Pal-Gly-Gln-Pro-Arg (SEQ ID NO: 3) | | 0.0003 |
| Ethanol | | 10.00 |
| Part D | | |
| Crillet 1 (Polysorbate 20) | Croda | 1.50 |
| Fragrance | — | 0.10 |

This formulation can be made according to the procedures generally outlined in Example 5.

Example 10

Lotion to Treat Dark Circles Under the Eyes

| Ingredients | | % by wt. |
|---|---|---|
| Part A | | |
| Ultrez 10 [Carbomer] | Noveon | 0.20 |
| Water Deionised | — | qs 100 |
| Part B | | |
| Glycerin | — | 3.00 |
| Part C | | |
| Potassium Sorbate | — | 0.10 |
| Part D | | |
| Volpo S10 [Steareth 10] | Croda | 1.50 |
| Crodafos CES [Ceterayl Alcohol Dicetyl Phosphate (and) Ceteth-10 Phosphate] | Croda | 3.00 |
| DC 200 [Dimethicone] | Dow Corning | 2.00 |
| Crodamol OSU [Diethylhexyl Succinate] | Croda | 5.00 |
| Mixed Parabens | — | 0.30 |
| Crill 3 [Sorbitan Stearate] | Croda | 0.40 |
| Part E | | |
| Sodium Hydroxide 38% | — | 0.20 |
| Water Deionised | — | 4.00 |
| Part F | | |
| Water | | 10.0 |
| Pal-Gly-His-Lys | | 0.0005 |
| Pal-Gly-Gln-Pro-Arg (SEQ ID NO: 3) | | 0.00025 |
| Deferoxamine | | 0.001 |
| Berberine | | 0.002 |

This formulation can be made according to the procedures generally outlined in Example 1 or 5. The combination of these 4 ingredients is destined to treat dark circles based on the fact that the iron chelator deferoxamine and the Berberine act together to eliminate haemoglobin residues, the peptides resynthesise tissue and thicken the skin. Deferoxamine can be replaced by EDTA, NTA, hydroxamic acids or other iron chelators in the appropriate amounts for efficient iron chelation. Berberine can be replaced by chrysine or similar flavonoids for the same purpose of stimulating the elimination of bilirubine.

Example 11
Anti-Stretchmark Gel

| Ingredients | | % by wt. |
|---|---|---|
| Part A | | |
| Water Deionised | — | qs 100 |
| Part B | | |
| Butylene Glycol | — | 5.00 |
| Phenova [Phenoxyethanol (and) Mixed Parabens] | Crodarom | 0.80 |
| Part C | | |
| Crill 3 [Sorbitan Stearate] | Croda | 1.20 |
| Crillet 3 [Polysorbate 60] | Croda | 3.00 |
| DC 200 [Dimethicone] | Dow Corning | 2.00 |
| Crodamol IPM [Isopropyl Myristate] | Croda | 5.00 |
| Crodamol W [Stearyl Heptanoate] | Croda | 0.30 |
| Crodamol GTCC [Caprylic/Capric Triglyceride] | Croda | 5.00 |
| Crodacol CS90 [Cetearyl Alcohol] | Croda | 2.00 |
| Part D | | |
| Carbopol 980 at 2% [Carbomer] | BF Goodrich | 10.00 |
| Part E | | |
| Potassium Sorbate | — | 0.10 |
| Part F | | |
| Water Deionised | — | 2.00 |
| Sodium Hydroxide | — | 0.20 |
| Part G | | |
| Water | | 10.0 |
| Pal-Gly-His-Lys | | 0.0003 |
| Pal-Gly-Gln-Pro-Arg (SEQ ID NO: 3) | | 0.00015 |
| Rutin | | 0.1 |
| Bowman Birk Inhibitor | | 0.0001 |

This gel can be prepared in the following way: Homogenize Part B and pour it into Part A. Heat Part (A+B) to 75° C. Heat Part C and Part D to 75° C. Pour Part C into Part (A+B) with helix stirring; then, pour Part D into Part (A+B+C). Add Part F and Part E. Pour Part G at about 35° C.

Rutin and Bowman Birk Inhibitor contribute to anti-stretchmark activity by allowing tissue regeneration, inhibiting protein breakdown and strengthening the crosslinks of collagen fibers. They can be replaced by similar flavonoids or protease enzyme inhibitors, respectively.

Example 12

Tissue Regeneration: Synergistic Effects of the Peptides

The tissue regenerating effect of the mixture of N-Palmitoyl-Gly-Gln-Pro-Arg (SEQ ID NO: 3) and N-Palmitoyl-Gly-His-Lys was established by the following experiment:

Normal human skin fibroblasts are cultivated in 24 well-plates in DMEM with 10% of FCS during 24 h, then rinsed. The cells then received the products to be tested in a medium DMEM without FCS containing ascorbic acid. The contact of cells with product was carried out during 3 days, then supernatants are taken and frozen. Each test included a negative control without solvent, a control solvent and a positive control ($10^E$-6% of TGF-β). Each determination was carried out n=3. Several repetitions independent of the tests were made. Assaying of the interesting molecules was carried out by Elisa (Collagen I & IV; Fibronectine) and by a calorimetric method (hyaluronic acid).

TABLE 1

Percentage of variation with respect to solvent
(0.08% DMSO in DMEM): 3 × 10E−4% ascorbic acid level.

| | | Collagen I | Fibronectin | Collagen IV | Hyaluronic Acid |
|---|---|---|---|---|---|
| TGF-β | $10^E$-6% | +91% | +176% | +4% | +43% |
| Pal KTTKS | 1 ppm | +8% | +24% | +6% | +3% |
| (SEQ ID NO: 5) | 2 ppm | +30% | +20 | +12% | +26% |
| | 4 ppm | +48% | +74% | +15% | +28% |
| | 8 ppm | +93% | +100% | +22% | +31% |
| Pal GQPR | 0.5 ppm | +4% | +1% | +5% | −4% |
| (SEQ ID NO: 3) | 1.5 ppm | −1% | +15% | −8% | +9% |
| | 2.5 ppm | +19% | +35% | −5% | −13% |
| | 3.64 ppm | +65% | +56% | −14% | −1% |
| Pal GHK | 1 ppm | +9% | +8% | +5% | +3% |
| | 3 ppm | −11% | +2% | −4% | +11% |
| | 5 ppm | +11% | −15% | +6% | 0% |
| | 7.3 ppm | −9% | +13% | −9% | −1% |
| Combination | 1 + 0.5 | +33% | +1% | −4% | +9% |
| | 3 + 1.5 | +67% | +41% | −10% | +11% |
| | 5 + 2.5 | +63% | +44% | −5% | +27% |
| | 7.3 + 3.64 | +256% | +147% | +20% | +92% |

Note that a single letter convention is used to identify the amino acids of each peptide. The base level, as established by control is 0%. Thus, activity over 0% shows stimulation of one or more of the tested biomolecules.

---

I claim:

1. A topical composition comprising:
   a) between about 0.00001% and about 0.5% w/w of at least one rigin-based tetrapeptide and between about 0.00001% and about 1.0% w/w of at least one GHK-tripeptide, wherein said tripeptide is present in an amount that is greater than the amount of said tetrapeptide by % w/w and/or wherein said tripeptide and said tetrapeptide are acyl derivatives; and
   b) at least one additional ingredient.

2. The topical composition of claim 1, wherein said tripeptide is present in an amount that is greater than the amount of said tetrapeptide by % w/w.

3. The topical composition of claim 1, wherein said tripeptide and said tetrapeptide are acyl derivatives.

4. The topical composition of any of claims 1, 2, or 3, wherein said tetrapeptide is N-palmitoyl-Gly-Gln-Pro-Arg (SEQ ID NO: 3).

5. The topical composition of any of claims 1, 2, or 3, wherein said tripeptide is N-palmitoyl-Gly-His-Lys.

6. The topical composition of claim 1, wherein said at least one additional ingredient is a cleaning agent, hair conditioning agent, skin conditioning agent, hair styling agent, antidandruff agent, hair growth promoter, perfume, sunscreen, sunblock, pigment, moisturizer, film former, hair color, make-up agent, detergent, pharmaceutical, thickening agent, emulsifier, humectant, emollient, antiseptic agent, deodorant active, dermatologically acceptable carrier, surfactant, abrasive, absorbent, fragrance, coloring/colorant, essential oil, skin sensate, astringent, anti-acne agent, anti-caking agent, antifoaming agent, antimicrobial, antioxidant, binder, biological additive, enzyme, enzyme inhibitor, enzyme activator, coenzyme, botanical extract, ceramide, addition peptide, buffering agent, bulking agent, chelating agent, cosmetic biocide, denaturant drug astringent, external analgesic, polymer, quat, substantivity increasing agent, opacifying agent, pH adjuster, propellant, reducing agent, sequestrant, skin bleaching agent, skin lightening agent, skin-conditioning agent, skin soothing agent, skin healing agent, aloe vera, pantothenic acid and derivative thereof, allantoin, bisabolol, dipotassium glycyrrhizinate, skin treating agent, thickener, or a vitamin or derivative thereof.

7. The topical composition of claim 6 further comprising a plurality of additional ingredients and wherein at least one of said additional ingredients is a dermatologically acceptable carrier.

8. The topical composition of claim 7, wherein at least one of said additional ingredients includes rutin or Bowman Birk Inhibitor.

9. The topical composition of claim 7, wherein said additional ingredients include a chelating agent, and either berberine or chrysine.

10. The topical composition of claim 3, wherein said acyl group is bound to the N-terminal end of at least one amino acid and is a straight-chain or branched-chain, long or short chain, saturated or unsaturated, substituted with one or more hydroxyl, amino, acyl amino, sulfate or sulfide groups or may be unsubstituted, and which can be derived from acetic acid, biotinic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid or mixtures thereof.

11. The topical composition of claim 10 wherein said acyl group is an acetyl group, palmitoyl group, elaidoyl group, myristyl group, biotinyl group or octanoyl group.

12. A method of reducing the visible signs of aging comprising: applying to skin in need of such treatment the topical composition of claim 1 to a portion of human skin showing signs of aging at least once a day for a period of time at least sufficient to provide a reduction in the visible signs of aging of that portion of human skin.

13. A method of reducing stretch marks comprising: applying to skin in need of such treatment the topical composition of claim 8 to a portion of human skin showing stretch marks at least once a day for a period of time at least sufficient to provide a reduction in the visible signs of stretch marks of that portion of human skin.

14. A method of reducing dark circles under the eyes comprising: applying to skin in need of such treatment the topical composition of claim 9 to a portion of human skin showing dark circles under the eyes at least once a day for a period of time at least sufficient to provide a reduction in the visible dark circles of that portion of human skin.

* * * * *